US010537676B2

(12) United States Patent
Barth et al.

(10) Patent No.: US 10,537,676 B2
(45) Date of Patent: Jan. 21, 2020

(54) SENSING SYSTEM FOR MEDICATION DELIVERY DEVICE

(71) Applicant: Eli Lilly and Company, Indianapolis, IN (US)

(72) Inventors: Phillip W. Barth, Portola Valley, CA (US); Mateusz B. Bryning, San Jose, CA (US); Leslie A. Field, Portola Valley, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/766,859

(22) PCT Filed: Oct. 27, 2016

(86) PCT No.: PCT/US2016/059099
§ 371 (c)(1),
(2) Date: Apr. 9, 2018

(87) PCT Pub. No.: WO2017/079027
PCT Pub. Date: May 11, 2017

(65) Prior Publication Data
US 2018/0296756 A1   Oct. 18, 2018

Related U.S. Application Data

(60) Provisional application No. 62/250,012, filed on Nov. 3, 2015.

(51) Int. Cl.
*A61M 5/168* (2006.01)
*A61M 5/172* (2006.01)

(52) U.S. Cl.
CPC .... *A61M 5/16886* (2013.01); *A61M 5/16836* (2013.01); *A61M 5/1723* (2013.01)

(58) Field of Classification Search
CPC .... A61M 5/16886; A61M 5/14; A61M 5/172; A61M 5/16831; A61M 5/16836; A61M 5/1723
(Continued)

(56) References Cited

U.S. PATENT DOCUMENTS

| 5,381,510 A * | 1/1995 | Ford | A61M 5/44 165/169 |
| 7,361,155 B2 * | 4/2008 | Sage, Jr. | A61M 5/168 604/65 |

(Continued)

FOREIGN PATENT DOCUMENTS

| WO | 2012166168 | 12/2012 |
| WO | 2014187432 | 11/2014 |

*Primary Examiner* — David P Porta
*Assistant Examiner* — Gisselle M Gutierrez
(74) *Attorney, Agent, or Firm* — Jonathan Anderson

(57) ABSTRACT

A fluid sensing system (30) including a fluid channel (32) with an inlet (34) and an outlet (36). A thermal device (38) is operably coupled thereto at a first position whereby thermal energy is transferable with fluid in the channel. A section of the fluid channel downstream of the first position has a predefined cross section and flow path. A thermal imaging device (46) is positioned to capture a thermal image of at least a portion of the downstream section. A processor (48) coupled with the thermal imaging device is configured to determine at least one output value representative of a property of the fluid medication or fluid flow using the thermal image. The output value may be the flow volume. In some embodiments, the fluid channel also defines a section upstream of the first position with the thermal imaging device capturing an image that includes at least portions of both the upstream and downstream sections.

34 Claims, 6 Drawing Sheets

(58) Field of Classification Search
USPC .................................................. 250/338.1
See application file for complete search history.

(56) References Cited

U.S. PATENT DOCUMENTS

| | | | | |
|---|---|---|---|---|
| 2005/0082480 | A1* | 4/2005 | Wagner | G01J 5/60 250/338.1 |
| 2006/0210255 | A1* | 9/2006 | Cassidy | A61M 5/445 392/470 |
| 2010/0114072 | A1* | 5/2010 | Iordanov | A61B 5/0008 604/890.1 |
| 2012/0060456 | A1* | 3/2012 | Treier | B01D 46/0001 55/497 |
| 2012/0291540 | A1* | 11/2012 | Cooke | A61M 5/16831 73/204.11 |
| 2014/0121636 | A1 | 5/2014 | Boyden et al. | |
| 2014/0340512 | A1* | 11/2014 | Tao | A61M 5/1411 348/135 |
| 2015/0196710 | A1* | 7/2015 | Bennett | A61M 5/168 324/663 |
| 2016/0339127 | A1* | 11/2016 | Ma | A61L 2/24 |
| 2017/0258993 | A1* | 9/2017 | Pizzochero | A61M 5/16831 |
| 2018/0172493 | A1* | 6/2018 | Speldrich | G01F 1/6842 |
| 2018/0313345 | A1* | 11/2018 | Lee | B01L 3/50273 |

* cited by examiner

SENSING SYSTEM FOR MEDICATION DELIVERY DEVICE

BACKGROUND OF THE INVENTION

The present invention pertains to fluid delivery devices, and, in particular, to a sensing system for determining volumetric flow or other characteristics of the fluid being delivered.

A variety of known types of devices are used to deliver fluid medication to a patient. Such delivery devices can be simple in design, such as a standard syringe that is manually operated to deliver medication through its attached needle, or can be more complicated in design, such as infusion pumps that deliver medication through a cannula.

For many delivery devices, the amount of fluid to be delivered during an intended use is less than the complete medication contents of that device. Especially for such delivery devices, being able to determine or check the amount of fluid actually delivered in a given use may be of high importance.

Many existing devices use a container or cartridge from which medication is forced by advancement of a plunger within the container barrel. Determining how far the plunger has moved, or how far an element driving the plunger has moved, may serve as a proxy for determining the volume of medication that has been delivered from the device. However, such a means of determining the volume may not always prove suitable, such as if the implementation is overly complex, or the plunger is subject to large deformation, or the movement of the driving element does not result in an output that is readily useable by, for example, an electronic dosing system.

Thus, it would be desirable to provide a sensing system, or a delivery device that employs such a sensing system, that can overcome one or more of these and other shortcomings of the prior art.

SUMMARY OF THE INVENTION

The present invention provides a fluid sensing system that can be used to determine a volumetric flow or other fluid or fluid flow property and which is suitable for use with a dispensing device such as a dispensing device used to inject a liquid medication into a living organism.

The invention comprises, in one form thereof, a fluid sensing system for a medication delivery device. The medication delivery device includes a reservoir adapted to contain a supply of a fluid medication and a discharge structure through which the fluid medication is discharged from the medication delivery device, the discharge structure being adapted to introduce the fluid medication into a patient. The fluid sensing system is disposed on the medication delivery device and includes a fluid channel communicating the fluid medication from an inlet to an outlet. The inlet is in fluid communication with the reservoir with the reservoir being disposed upstream of the inlet. The outlet is in fluid communication with the discharge structure with the discharge structure being disposed downstream of the outlet. A thermal device is operably coupled with the fluid channel at a first position between the inlet and the outlet whereby thermal energy is transferable between the thermal device and the fluid medication flowing in the fluid channel at the first position. A downstream section of the fluid channel downstream of the first position has a predefined cross section and a predefined flow path. A thermal imaging device is positioned to capture a thermal image of at least a portion of the downstream section of the fluid channel and a processor is coupled with the thermal imaging device and configured to determine, based on at least one thermal image, at least one output value that is representative of a property of the fluid medication and/or the fluid flow in the fluid channel.

In some embodiments, the fluid medication is a liquid which, in some embodiments, may be adapted for injection into a living organism.

The fluid sensing system may also include an upstream section of the fluid channel upstream of the first position which has a predefined cross section and a predefined flow path wherein the thermal imaging device is positioned to capture a thermal image including at least a portion of the upstream section as well as a portion of the downstream section. In such a system including an upstream section, the downstream section and the upstream section of the fluid channel may define a serpentine flow path. Alternative embodiments may alternatively define a spiral or helix shaped flow path.

In still other embodiments, the thermal imaging device is spaced from and fixed relative to the fluid channel. In such an embodiment, the thermal imaging device may be adapted to capture a two-dimensional image defining an aspect ratio wherein the fluid channel is disposed in a plane and defines a serpentine flow path between the inlet and the outlet; the serpentine flow path defining an overall length and overall width in the plane wherein the ratio of the overall length and overall width are substantially equivalent to the aspect ratio and the thermal imaging device is positioned to capture an image containing substantially all of the serpentine flow path between the inlet and the outlet.

In still other embodiments, the fluid sensing system has a fluid channel that is disposed on a substantially planar first layer of material. In such an embodiment, the system may further include second and third layers of material defining the fluid channel, wherein the first, second and third layers each have a substantially consistent thickness with the second layer being disposed on the first layer and having a void defining the fluid channel and the third layer being disposed on the second layer opposite the first layer whereby the first layer and the third layer enclose the void defined by the second layer. In such embodiments having first, second and third layers of material, one of the first and third layers may take the form of a glass substrate. It is also possible to employ a plastic substrate.

In yet other alternative embodiments of the fluid sensing system wherein first, second and third layers form the fluid channel, the second layer may advantageously have a thickness within a range of 100 µm to 500 µm. In such an embodiment, the fluid channel may have a height substantially equivalent to the thickness of the second layer and a width of approximately 2 mm.

Various other embodiments are also possible, for example, one of the first and third layers may take the form of a thin film layer. Such a thin film layer may be advantageously formed out of a polylactic acid (PLA) film, e.g., a 25 µm thick film.

In still other embodiments of the fluid sensing system wherein first, second and third layers form the fluid channel, the first layer may be a layer substantially transparent to infrared light with the thermal imaging device being positioned to capture an image facing the first layer. In such an embodiment, the substantially transparent layer may be formed out of silicon, polydimethylsiloxane (PDMS), germanium, zinc selenide, silicon nitride (conventional or low stress), thin film cyclo olefin polymer, thin film cyclo olefin copolymer or other suitable material. Cyclo olefin polymers and cyclo olefin copolymers, such as those available under the tradenames Zeonor and Zeonex, may also be used to form a substantially transparent layer. In this regard, it is noted that cyclo olefin polymers and copolymers are not entirely transparent to infrared light in the typical range of thermal imaging devices, a sufficiently thin film of such material will be suitably transparent. Similarly, many materials not typically considered infrared transparent, will be infrared transparent when formed in a sufficiently thin film.

In yet other embodiments of the fluid sensing system wherein first, second and third layers form the fluid channel, the first layer may be a thermally conductive layer substantially opaque to infrared light with the thermal imaging device being positioned to capture an image facing the opaque layer. In such an embodiment, the opaque layer may be formed out of metals, polymers, ceramics, glass, polymer-ceramic composites or other suitable material.

In other embodiments of the fluid sensing system, the thermal device may be thermally coupled with an exterior surface of the fluid channel whereby thermal energy is transferred between the thermal device and the fluid medication through a wall of the fluid channel. In such an embodiment, the thermal device and thermal imaging device may be advantageously positioned on opposite sides of the fluid channel.

In some embodiments of the fluid sensing system the thermal device communicates thermal energy to the fluid medication in the fluid channel to thereby increase the temperature of the fluid medication. In such an embodiment, the thermal device may advantageously take the form of an electrical resistor. Alternative embodiments may employ other forms of thermal devices such as a light emitting diode (LED) or laser.

In still other embodiments of the fluid sensing system, the at least one output value advantageously includes a flow volume of the fluid medication. In yet other embodiments of the fluid sensing system, the at least one output value includes a volumetric flow rate of the fluid medication, an identity of the fluid medication, a concentration of a substance in the fluid medication, a temperature of the fluid medication, a heat capacity of the fluid medication, a pressure of the fluid medication, a viscosity of the fluid medication and/or a density of the fluid medication. An additional sensor, such as a fluid pressure, may be added to the system to thereby measure a second fluid property and thereby aid in the determination of the various fluid parameters.

In some embodiments of the fluid sensing system, the fluid channel forms a helical coil and the thermal imaging device is positioned to capture discrete discontinuous portions of the downstream section of the fluid channel. In such embodiments having a helical fluid channel, the reservoir may have a columnar shape with the helical coil formed by the fluid channel being wrapped about at least a portion of the reservoir.

In still other embodiments of the fluid sensing system, the system may additionally include a second sensing device wherein the second sensing device is operably coupled with the fluid medication between the reservoir and the discharge structure such that the second sensing device is adapted to measure a property of the fluid medication. The second sensor may advantageously take the form of a fluid pressure sensor such as a micro electro-mechanical system (MEMS) fluid pressure sensor.

In yet other embodiments of the fluid sensing system, the discharge structure may be disengageable from the medication delivery device whereby the discharge structure is disposable after a single use. For example, the discharge structure may be an injection needle which is detached and discarded after use. In such an embodiment, the fluid channel may be supported on the reservoir with the thermal imaging device and processor being non-destructively separable from the reservoir and the fluid channel. This allows the reservoir and fluid channel to be disposed of after the contents of the reservoir have been depleted while re-using the thermal imaging device and processor.

In some embodiments, the discharge structure advantageously takes the form of a hollow needle adapted to be inserted into a living organism whereby the fluid medication can be injected into the living organism.

In some embodiments, the reservoir includes a feature having a thermally unique signature and whereby the identity or authenticity of the reservoir and its contents can be checked with the thermal imaging device.

In some embodiments, the fluid sensing system includes a substrate structure defining the fluid channel wherein the substrate structure also defines at least one insulative void. In such an embodiment, the insulative void may define a slot that extends entirely through the substrate structure. For an embodiment with an insulative void, the embodiment may include a plurality of such insulative voids and the fluid channel may define a serpentine path having a plurality of parallel path segments and wherein at least one of the plurality of insulative voids is disposed between each pair of adjacent path segments.

One advantage of the present invention is that a system for sensing volumetric flow may be provided for a medication delivery device.

Another advantage of the present invention is that a system for sensing volumetric flow may be provided for a medication delivery device in which no sensors need be placed in contact with the medication. The use of non-contact components also facilitates the potential re-use of such non-contact components.

Another advantage of the present invention is that a system for sensing characteristics of a medication in a delivery device may be provided in a compact and convenient fashion.

BRIEF DESCRIPTION OF THE DRAWINGS

The above mentioned and other features of this invention, and the manner of attaining them, will become more apparent and the invention itself will be better understood by reference to the following description of an embodiment of the invention taken in conjunction with the accompanying drawings, wherein.

Figure 1:
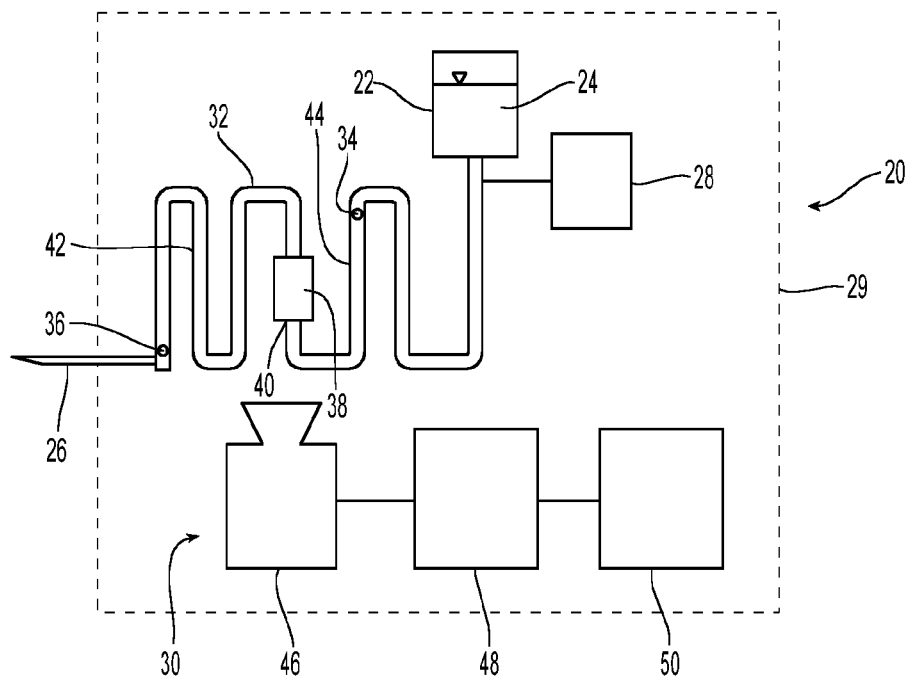
FIG. 1 is a schematic representation of a delivery device employing a fluid sensing system.

Corresponding reference characters indicate corresponding parts throughout the several views. Although the exemplification set out herein illustrates a embodiments of the invention, in several forms, the embodiments disclosed below are not intended to be exhaustive or to be construed as limiting the scope of the invention to the precise forms disclosed.

DETAILED DESCRIPTION OF THE INVENTION

A medication delivery device 20 is schematically depicted in FIG. 1. Medication delivery device 20 take various forms such as an injection device, e.g., an injection pen, an infusion device, e.g., an infusion pump, or other device for providing a medication fluid to a patient. Medication delivery device 20 includes a reservoir 22 containing a supply of the fluid 24 to be dispensed by device 20. In the illustrated example, fluid 24 is a liquid medication intended to be injected into a living organism. In some embodiments, reservoir 22 may take the form of a disposable cartridge containing one or more doses of a liquid medication such as insulin.

As can also be seen in FIG. 1, device 20 includes a discharge structure 26 through which the fluid medication 24 is expelled. In the illustrated example, structure 26 is a hollow needle which can be inserted into a living organism to thereby allow fluid medication 24 to be injected into the organism. For example, the living organism might be a human being who has diabetes and requires periodic injections of insulin. A driving mechanism 28 is coupled with the fluidic system and provides the means for causing fluid to flow from reservoir 22 toward discharge structure 26. Various driving mechanisms 28 may be used depending upon the application for which device 20 is adapted. For example, driving mechanism 28 might advantageously take the form of an electrically powered infusion pump. Although it will often be desirable to employ an automated driving mechanism 28, it would also be possible to employ a spring driven or manually operated plunger for discharging the contents of reservoir 22.

Device 20 also includes a fluid sensing system 30 which senses the flow of fluid and, in the illustrated embodiment, does not require contact with the fluid. Fluid sensing system 30 is disposed on device 20, for example, it may be located entirely or partially within the housing of device 20. Fluid sensing system 30 is disposed between reservoir 22 and discharge structure 26 to thereby measure and/or monitor a fluid flow parameter of the flow of fluid medication 24 from reservoir 22 to discharge structure 26. For example, sensing system 30 could be used to measure or monitor the volumetric flow or flow volume of fluid medication 24. In other words, it can be used to measure the total volume of fluid medication 24 that flows past the point being monitored. When the fluid flow is not diverted and there are no intermediate reservoirs, a measurement of the flow volume will also correspond to the volume of fluid medication 24 discharged through discharge structure 26. This measurement can be particularly useful when device 20 is used to dispense a fluid medication where the dispensed quantity is of significant importance. Sensing system 30 can also be used to measure or monitor the volumetric flow rate of fluid medication 24. This can be useful for control purposes, and, when combined with the elapsed time of the flow, the measurement is also useful to determine the volume of fluid discharged through discharge structure 26. The measurement of flow volumes and volumetric flow rates by sensing system 30 is discussed in greater detail below.

Fluid sensing system 30 includes a fluid channel 32 that communicates fluid medication 24 from an inlet 34 to an outlet 36. As can be seen in FIG. 1, reservoir 22 is disposed upstream of inlet 34 and discharge structure 26 is disposed downstream of outlet 36. In some embodiments, inlet 34 and outlet 36 may be distinct physical structures. In other embodiments, however, inlet 34 and outlet 36 are simply non-distinct points on a continuous fluid channel demarking that portion of the fluid channel associated with fluid sensing system 30.

A thermal device 38 is coupled with fluid channel 32 at a location 40 between inlet 34 and outlet 36. Downstream of location 40 is a downstream section 42 of fluid channel 32 that extends from location 40 to outlet 36. Upstream of location 40 is an upstream section 44 that extends from inlet 34 to location 40.

A thermal device 38 is operably coupled with fluid channel 32 at location 40 to provide for the transfer of thermal energy between the thermal device 38 and fluid medication 24 flowing in the fluid channel 32 at location 40. Thermal device 38 could be either a heating or cooling device. For example, thermal device 38 could be cooling device that absorbs thermal energy from fluid medication 24 to thereby cool the fluid. Such a cooling device might include a heat pipe or a thermal heat sink which has been cooled to a temperature below that of the fluid in reservoir 22.

Figure 3:
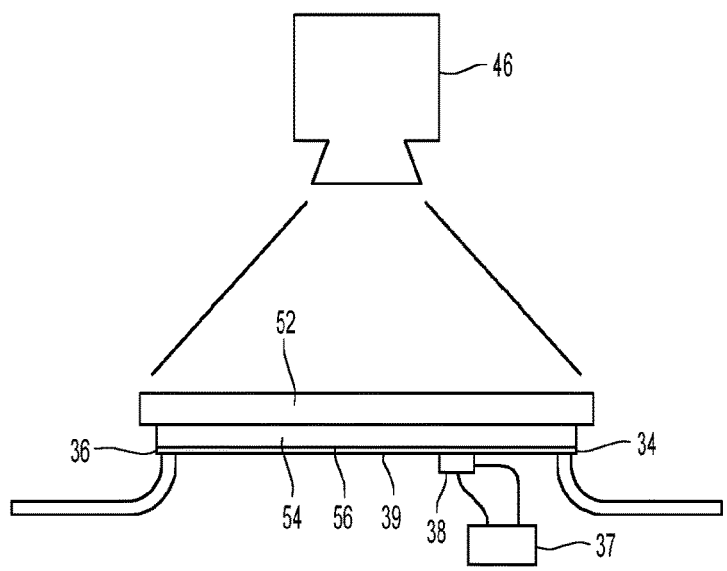
FIG. 3 is a schematic side view of a fluid sensing system.

Alternatively, thermal device 38 could be a heating device that communicates thermal energy to the fluid medication 24 in the fluid channel 32 at location 40 to thereby increase the temperature of the fluid medication 24. For example, in the illustrated example, thermal device 38 is an electrical resistor that experiences a temperature increase and transfers thermal energy to fluid medication 24 when electrical current is passed therethrough. In the illustrated embodiment (FIG. 3), an electrical power supply 37, for example, a battery, supplies electrical current to resistor 38 which is a 200 Ohm resistor. Processor 48 is advantageously coupled with power supply 37 to regulate the supply of electrical current to resistor 38.

Various other alternative devices may be used to provide a thermal device 38. For example, a Peltier (thermoelectric) device (TEC), a light source such as a laser or LED, or a passive mechanism such as the body heat of the user could be employed to provide a thermal device 38.

Thermal device 38 can be thermally coupled with fluid medication 24 by thermally coupling it with the exterior surface 39 of fluid channel 32 whereby thermal energy is transferred between thermal device 38 and fluid medication 24 through a wall 33 of fluid channel 32. For example, electrical resistor 38 can be attached to exterior surface 39 of fluid channel 32 to thereby communicate thermal energy to fluid medication 24 through fluid channel wall 33. Alternatively, a thermal device 38 could be integrated into the fluid channel structure and form a portion of the interior surface of the fluid channel and thereby provide for the direct transfer of thermal energy between thermal device 38 and fluid medication 24. In yet other embodiments, the thermal device 38 may be spaced from fluid channel 32 to provide for non-contact thermal transfer. For example, thermal device 38 could be a laser or LED to provide for non-contact heating.

Thermal device 38 is used to create a local variation in the temperature of the fluid flowing in fluid channel 32. For example, fluid medication 24 in reservoir 22 might be at the ambient temperature and thermal device 38 will either raise or lower the temperature of fluid medication 24 at location 40. The temperature of fluid medication 24 would then move toward the ambient temperature as it flows downstream from location 40. For some applications, the system may be designed so that the fluid returns to ambient temperature by the time it reaches outlet 36. In some applications, however, fluid medication 24 in reservoir 22 may be at a temperature that differs from the ambient temperature, e.g., fluid medication 24 might be maintained in a chilled condition prior to injection. In such applications, it might also be desirable to employ a heating element between fluid sensing system 30 and discharge structure 26 to bring the fluid to the desired temperature before discharge.

For example, in some applications, it may be desirable to inject fluid medication 24 at body temperature which is typically much higher than the ambient temperature. In such an application, the fluid medication 24 may have a temperature greater than the ambient temperature when it reaches location 40 where it is either heated or chilled. It will move then begin moving toward ambient temperature. The initial temperature of the fluid and the amount of heat either added or removed at location 40 can be selected such that the fluid is at the desired temperature when it is discharged regardless of whether the desired temperature at discharge is the ambient temperature or some other temperature.

Depending upon the fluid flow parameters being measured with system 30 and the application of system 30, thermal device 38 may be used to provide either constant heating or cooling or a pulsed heating or cooling. The use of pulsed heating/cooling may be useful in preventing the degradation of pharmaceutical compounds or other sensitive fluids.

The magnitude of the local temperature variation generated by thermal device 38 will vary depending upon the particular application of system 30. For example, sensitivity and resolution of the imaging device 46 will have an impact on the magnitude of the temperature variation best suited for a particular application. It is anticipated that a maximum magnitude of the local temperature variation which would be sufficient is on the order of less than 10° C. In some applications, the magnitude of the local variation may be as small as 1° C. or even a fraction of 1° C. In other embodiments, the magnitude of the variation could exceed 10° C.

In some applications, a feedback loop may be beneficially employed with thermal device 38. Such a feedback loop could monitor the temperature of thermal device 38 and adjust the operating parameters thereof, e.g., current flowing to a resistor, to ensure stable operation. This type of feedback loop could be integrated into sensing system 30 using processor 48 and thermal imaging device 46 as the monitoring device. Alternatively, a separate circuit that includes a thermocouple and an independent controller could be used. Some applications might also benefit from the use of high-precision temperature control methods such as the use of a proportional-integral-derivative (PID) controller for temperature control.

A thermal imaging device 46 is positioned to capture a thermal image of at least a portion of the downstream section 42 of fluid channel 32. A processor 48 is coupled with thermal imaging device 46 and is configured to determine at least one output value as a function of the thermal image as discussed in greater detail below. In other words, the thermal image is processed to assess a characteristic of the fluid in channel 32. Advantageously, this analysis of the thermal image will determine the flow volume and/or volumetric flow rate of fluid medication 24 in channel 32.

The output value may optionally be communicated to a user with an output device 50 such as a display, e.g., a liquid crystal display (LCD) screen. Alternatively, the output value may be used by processor 48 for another purpose, e.g., the system may determine the heat capacity of the fluid to assess the concentration of active medication in a fluid carrier, without communicating the value to the user.

Thermal device 38 can be positioned either in or outside the field of view of thermal imaging device 46. By placing the thermal device outside the field of view, the imaging artifacts and interference potentially caused by thermal device 38 can be reduced. Regardless of whether or not the thermal imaging device 38 is within the field of view of thermal imaging device 46, it will generally be advantageous to include at least a portion of both the downstream 42 and upstream section 44 of the fluid channel 32. The inclusion of at least a portion of the upstream section 44 can be useful for purposes of providing a reference temperature for calibration.

Figure 2:
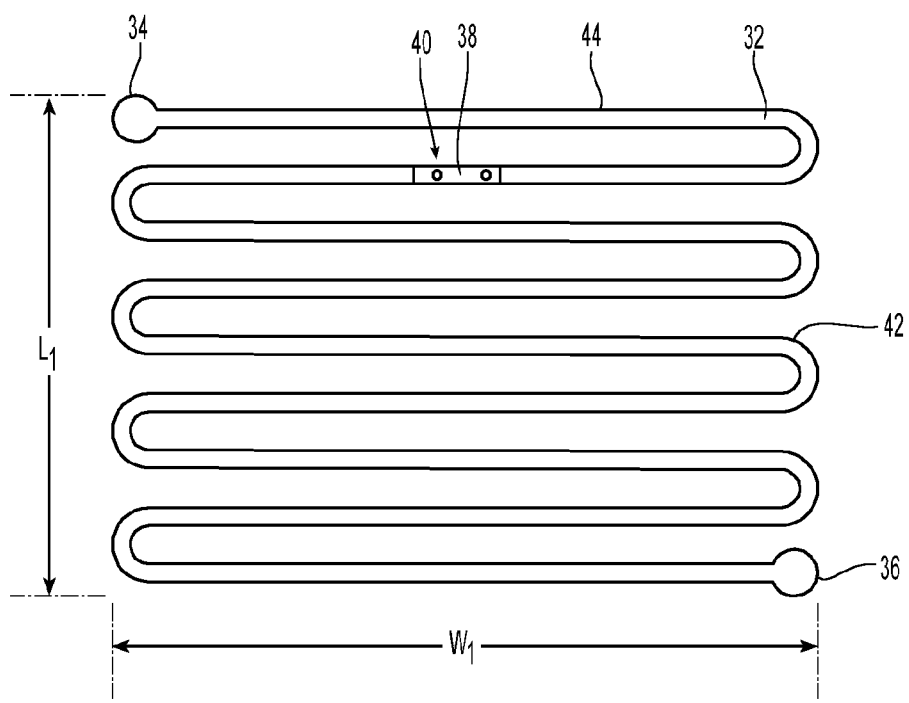
FIG. 2 is a top view of a fluid channel and heating device for use in fluid sensing system.

It is noted that by extending one leg of the serpentine path shown in FIG. 2 beyond the limits of the field of view, thermal device 38 could be placed outside the field of view while still including a substantial portion of both upstream and downstream sections of channel 32 in the field of view. Alternatively, thermal device 38 and thermal imaging device 46 can be positioned on opposite sides of fluid channel 32 as schematically depicted in FIG. 1 to limit the interference of thermal device 38 itself when capturing a thermal image with device 46. In the illustrated embodiment, the thermal imaging device 46 is spaced from and fixed relative to fluid channel 32 such that the portion of fluid channel 32 captured in the images remains constant. For example, both thermal imaging device 46 and fluid channel 32 can be fixed relative to housing 29 or other common structure.

Figure 5:
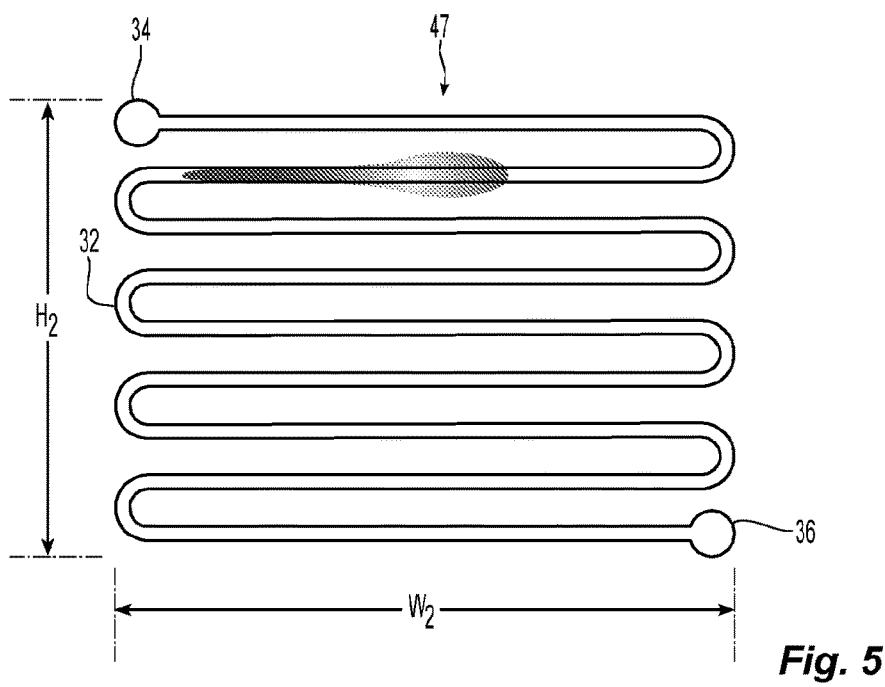
FIG. 5 is a schematic representation of an infrared image for use in a fluid sensing system illustrating a low flow rate.
Figure 6:
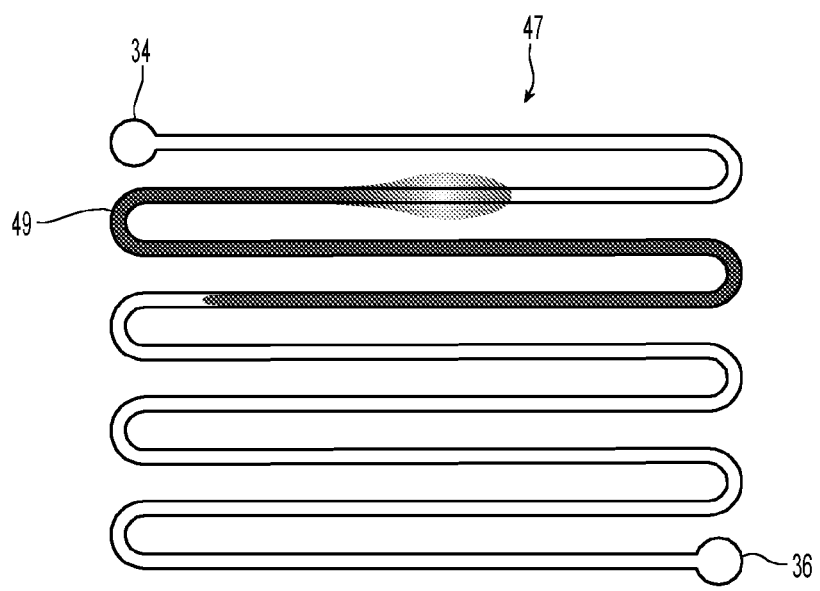
FIG. 6 is a schematic representation of an infrared image for use in a fluid sensing system illustrating a medium flow rate.
Figure 7:
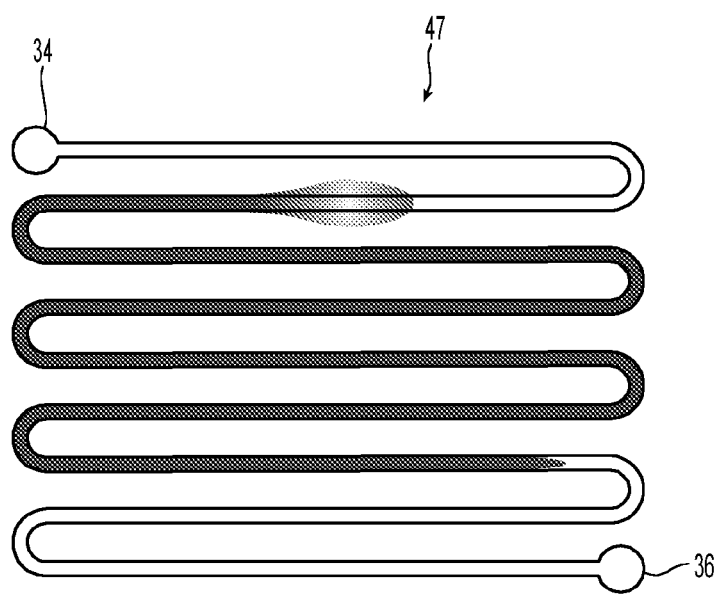
FIG. 7 is a schematic representation of an infrared image for use in a fluid sensing system illustrating a high flow rate.

As best seen in FIGS. 2 and 5-7, in the illustrated embodiment, fluid channel 32 defines a flow path having a serpentine shape. This shape is advantageous because it allows a longer length of the flow path to be captured in a single thermal image. In the exemplary embodiment, thermal imaging device 46 captures a two-dimensional thermographic image 47 representing the radiation in the infrared range of the objects in the field of view. FIGS. 5-7 are schematic representations of such images 47.

Like a conventional camera, device 46 has an aspect ratio that corresponds to the ratio of the height ($H_2$) to width ($W_2$) of image 47 captured by device 46 (FIG. 5). A typical aspect ratio might be 3:4. By configuring fluid conduit 32 to lie in a plane and have a serpentine shape with an overall length ($L_1$) and an overall width ($W_1$) (FIG. 2) such that the ratio of $L_1/W_1$ is substantially equivalent to $H_2/W_2$ and positioning thermal imaging device 46 to face perpendicular to the plane of channel 32 at an appropriate distance from fluid channel 32, substantially all of the serpentine flow path between inlet 34 and outlet 36 can be captured in thermal image 47 without any significant wasted image potential. While the use of a serpentine shape provides advantages, alternative configurations, such as a spiral or linear flow path, can alternatively be used.

The most suitable shape for the fluid channel will depend upon a number of factors, most significantly the anticipated flow rate. For example, the serpentine shape depicted in FIGS. 2 and 5-7 is well-suited for determining flow volume and flow rate in medium to high flow rates applications. A linear flow path is well suited for determining flow volume and flow rate in a low flow rate application. A three-dimensional helical coil configuration for the flow path where discrete non-continuous sections of the flow path are imaged may be useful when determining flow volume and flow rate for relatively high flow rates. When fluid properties other than flow volume and flow rate are being assessed, it may be beneficial to include additional or alternative features in the flow channel. For example, it may be advantageous to use a relatively wide channel that includes obstacles or features such as pillars in the flow channel or irregular or serrated side walls to thereby impact the flow and facilitate obtaining additional data. A side chamber in communication with the flow channel and which includes a second sensing device such as a pressure sensor could also be employed. Such additional features and sensing device may be particularly helpful when determining fluid properties beyond the flow volume and flow rate such as the viscosity, pressure or other property.

Thermal imaging device 46 can take the form of an infrared (IR) camera. Such IR cameras are commercially available and can be adapted for use in system 30. For example, IR cameras are commercially available that can be connected with a smart phone to capture thermal images. Also commercially available are IR camera chips that can be incorporated into applications without requiring connection to a smart phone. For example, an IR camera chip sold under the trademark Lepton® is commercially available from FLIR Systems, Inc. and can be used in fluid sensing system 30. Some of the factors that will influence the selection of the thermal imaging device 46 will be whether the size of the device (smaller will generally be more desirable), the power requirements of the device (low electrical power requirements will generally be more desirable), the thermal sensitivity and the resolution (number of pixels) are adequate for the intended application. The determination of some fluid properties will require a greater thermal sensitivity and/or resolution than other fluid properties. For example, if the sensing system is used to determine a concentration or identity of the fluid, it will require a greater thermal sensitivity and resolution than if it is merely used to determine a flow volume or flow rate. A second sensor, such as a fluid pressure sensor, might also be necessary for determining some fluid properties beyond the flow volume and flow rate. The use of one or more additional sensors may also allow for the selection of a thermal imaging device having a lower resolution. Such sensors could include any number of different known fluid sensors in addition to a fluid pressure sensor that might be useful for a particular application.

It is additionally noted, that most commercially available thermal imaging devices have thermal sensitivities on an order of magnitude of 0.01° C. and will have the necessary thermal sensitivity for use in the devices described herein. Commercially available thermal imaging devices can be obtained in a range of different resolutions with higher resolution devices being more expensive. As a result, it will generally be desirable to use a thermal imaging device with the lowest resolution that is adequate for the intended application.

In the exemplary embodiment, thermal imaging device 46 is a FLIR Lepton® having a spectral range in the longwave infrared spectrum of approximately 8 μm to approximately 14 μm; a thermal sensitivity of less than 50 mK (0.050° C.) and an output format that is user selectable and may be 14-bit, 8-bit (AGC applied), or 24-bit RGB (AGC and colorization applied).

Returning to a discussion of fluid channel 32, it is noted that in the illustrated example, middle layer 54 defines the plane in which fluid channel 32 is disposed. Alternative arrangements to provide for a substantially planar serpentine flow path, however, may also be used to maximize the utilization of the imaging capabilities of device 46. To maintain the shape of the flow path in a predefined configuration, it will often be desirable to mount or form the fluid channel on a rigid substrate.

In the exemplary embodiment, a multi-layered structure is used to form fluid channel 32 and maintain its shape. The structure of the exemplary embodiment is best understood with reference to FIGS. 3 and 4. In this embodiment, fluid channel 32 is defined by three layers of material. More specifically, the illustrated example includes a relatively thick outer layer 52, a center layer 54 and a thin film outer layer 56. Outer layer 52 functions as a rigid planar substrate for fluid channel 32. By having fluid channel 32 disposed on a substantially planar, rigid structure, it maintains the predefined shape of the flow path to facilitate capturing thermal images thereof.

A void 58 is formed in middle layer 54 to define the layout and width of fluid channel 32. Outer layers 52, 56 are disposed on the opposite sides of middle layer 54 whereby layers 52, 56 enclose the void 58 formed in middle layer 54 and thereby define fluid channel 32. In the illustrated embodiment, layers 52, 54 and 56 are each substantially planar and have differing thicknesses. Alternative embodiments, however, may employ either greater or fewer layers and wherein some or all of the layers have a substantially constant thickness.

In the illustrated embodiment, layer 52 is a substantially planar layer of material which takes the form of a glass substrate. The use of a glass substrate provides a planar rigid structure that maintains fluid channel 32 in a predefined shape. Alternative embodiments, however, can utilize other structures to maintain the configuration of fluid channel 32. For example, instead of relying upon the rigidity of a single layer of material, the combined structural strength of two or more of the layers forming channel 32 could provide the rigidity to maintain the shape of fluid channel 32. Still other methods could also be employed, for example, a flexible fluid channel could be fixed to a rigid support member. While it will generally be desirable to maintain fluid channel 32 in a plane to facilitate the processing of the thermographic images, it is not essential for fluid channel 32 to be maintained in a plane and, particularly if other considerations dictate an alternative arrangement, a non-planar configuration of fluid channel 32 could be employed. An example of such a non-planar configuration is discussed below when describing the embodiment of FIGS. 10 and 11.

Figure 4:
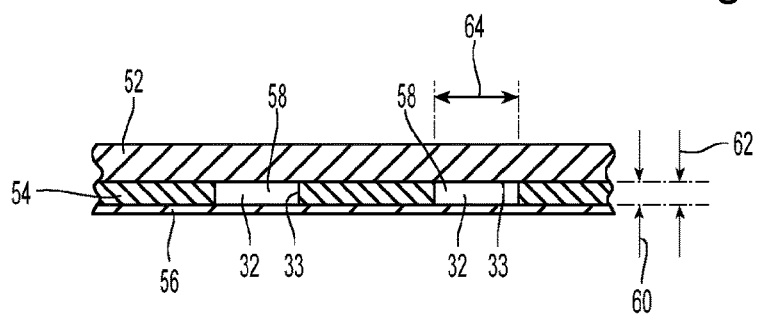
FIG. 4 is a schematic cross section through a portion of the fluid sensing system fluid channel.

In addition to a predefined flow path shape, fluid channel 32 also has a predefined cross sectional shape (FIG. 4). The cross sectional shape of channel 32 can vary or remain constant over the length of the fluid channel 32. The desirability of maintaining a constant cross sectional shape will depend in part on the fluid flow parameters which will be determined based upon the thermographic images captured by device 46. In the exemplary embodiment, the cross sectional shape and area is maintained substantially constant over the length of fluid channel 32 between inlet 34 and outlet 36.

In the exemplary embodiment, it is the void space 58 in layer 54 that defines the layout of the flow path and width of channel 32 while the two outer layers 52, 56 define the height of the substantially rectangular fluid channel 32. As discussed above, the layout of the flow path defines a serpentine shape in the illustrated embodiment. In the exemplary embodiment, middle layer 54 has a thickness 60 of approximately 100 µm. Because void 58 extends the full thickness of layer 54 without extending beyond the limits of layer 54, fluid channel 32 has a height 62 substantially equivalent to the thickness 60 of middle layer 54. The width 64 of channel 32 is approximately 2 mm in the illustrated embodiment. For the exemplary embodiment, channel 32 maintains a substantially constant cross sectional shape having the approximate dimensions of 100 µm by 2 mm for the entire length of downstream section 42 and upstream section 44.

The optimal dimensions of the fluid channel will depend significantly upon the anticipated flow rate of the fluid through the channel. For example, when using a medical delivery device to inject a liquid medicament into a patient, the flowrate will often be between 0.5 milliliter/minute and 15 milliliter/minute. At this flowrate, a channel having a width of 2 mm and a depth within the range of 100 µm to 500 µm will often be suitable. For many such applications involving the injection of a liquid medicament, the length of such a fluid channel within the field of view of the imaging device may advantageously be between 200 mm and 250 mm. For example, a suitable channel might have a width of 2 mm, a depth of 500 µm and a length of 222 mm.

It is further noted that when using a serpentine flow channel, the distance separating the parallel sections of the flow channel is subject to competing design objectives. Reducing the distance between the parallel sections of fluid channel helps to minimize the footprint of the sensing system and maximize the length of the flow channel within the field of view of the imaging device. However, if the distance becomes too small, thermal interference between adjacent fluid sections can arise. Reducing the separation distance between channel sections can also increase manufacturing costs. When using a channel having a width of 2 mm and a depth of 500 µm, a separation distance of 3 mm balances many of the competing design objectives and allows the channel to be cost effectively manufactured using laser machining.

Middle layer 54 may be formed out of a metal, silicon, or other suitable material. A thin film layer may be used to form an outer layer 56. For example, layer 56 may be formed using a polylactic acid film. Alternatively, layer 56 and/or layer 52 could be formed using a cyclic olefin compound or a cyclic olefin copolymer. As discussed in greater detail below, one of the outer layers 52, 56 is adapted to facilitate the capture of a thermographic image that is representative of the thermographic profile of fluid medication 24 flowing within channel 32.

Middle layer 54 forming fluid channel 32 advantageously acts as a thermal insulator inhibiting the transfer of heat from one leg of channel 32 to an adjacent leg of channel 32. Advantageously, middle layer 54 has lower thermal conductivity than the outer layer 52 or 56 which faces thermal imaging device 46. The outer layer 52 or 56 opposite thermal imaging device 46 may also advantageously have a thermal conductivity that is lower than the outer layer facing thermal imaging device 46. By providing the middle layer 54 and the outer layer opposite thermal imaging device 46 with greater thermal insulative properties relative to the outer layer facing thermal imaging device 46, the transfer of thermal energy between adjacent legs of channel 32 is less likely to occur. This, in turn, provides a better thermal profile for capture by thermal imaging device 46. For some applications, it might also be advantageous for one of the layers to form or be in thermal communication with a heat sink. For example, such a layer might be positioned on the opposite side of thermal imaging device 46 and facilitate the achieving of the desired discharge temperature of the fluid.

Middle layer 54 can be provided with enhanced thermal insulative properties by infusing an insulative material in layer 54 or providing layer 54 with an insulative coating. Similarly, the outer layer opposite thermal imaging device 46 could be infused or coated with an insulative material. If an insulative coating is used, it is advantageously applied to at least the channel walls 33 defined by middle layer 54 and the outer layer disposed opposite thermal imaging device 46. Various different materials, such as polymers, adhesives with insulative properties, or other conventional coating materials having suitable physical properties may be used. Conventional coating technologies can be used to apply the coating such as spray, spin, sputtering and plasma coating applications. The various forms of vacuum coating technologies, such as chemical vapor deposition (CVD), plasma enhanced chemical vapor deposition (PECVD) and the like, may also be used. Conventional screen printing techniques may be used to control the application of the coating to the desired location. MEMS (microelectromechanical systems), microfluidic, and IC (integrated chip) manufacturing techniques may also be used to manufacture the fluid channel and supporting substrate.

Figure 12:
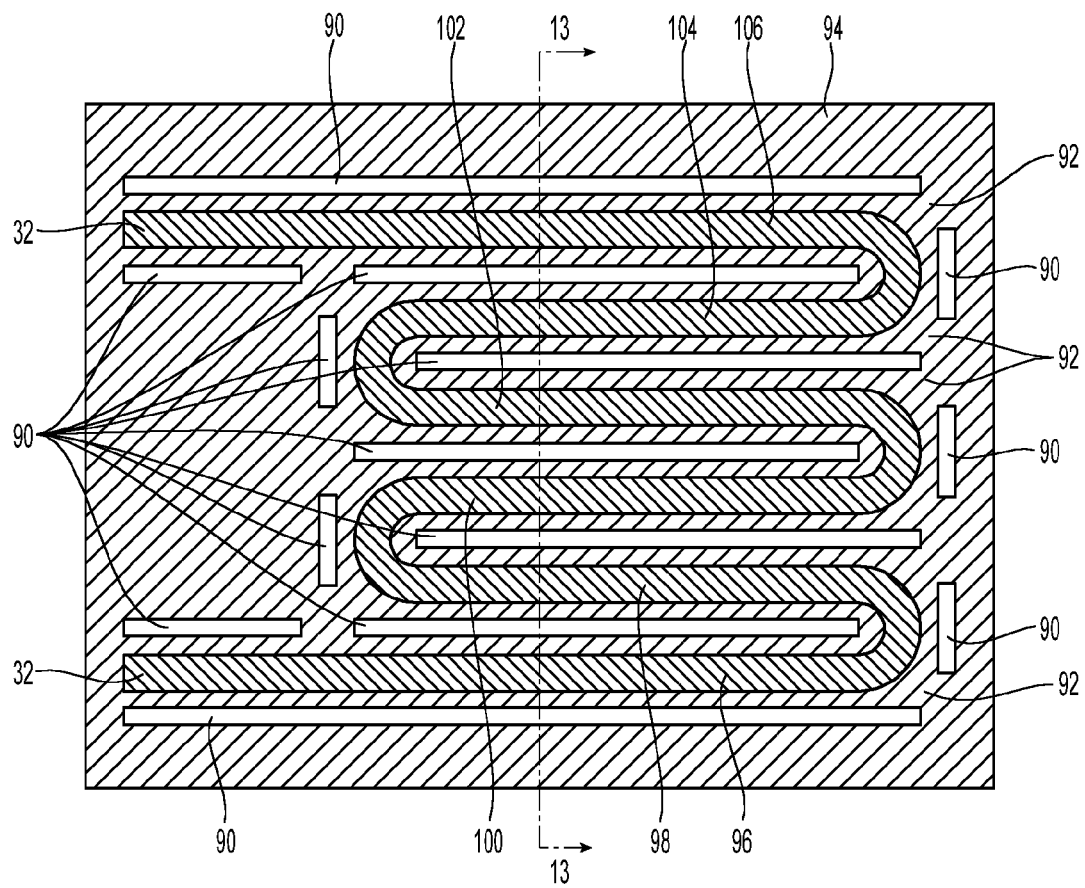
FIG. 12 is a schematic representation of another fluid sensing system.
Figure 13:
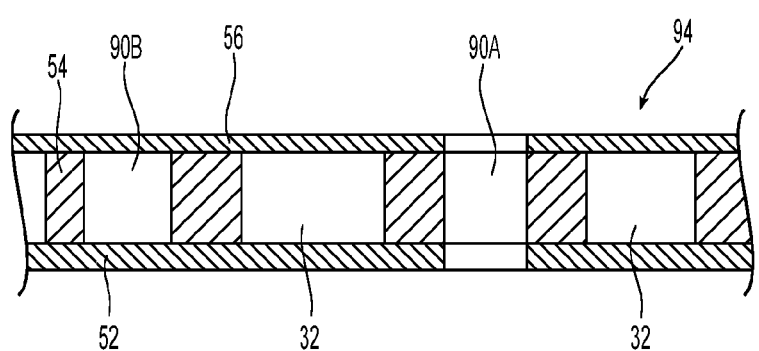
FIG. 13 is a schematic cross section of the fluid sensing system taken along line 13-13 of FIG. 12.

FIGS. 12 and 13 illustrate an alternative embodiment which utilizes voids in the rigid substrate forming the fluid channel to enhance the thermal isolation of discrete sections of the fluid channel. When an enclosed fluidic channel 32 meanders back and forth to form a serpentine path within a generally planar substrate in order to maximize the fluid path length visible to a camera, the problem of interactions between adjacent legs of the serpentine channel can arise. If the camera is an infrared camera which senses the temperature of the fluid, or which senses the temperature of the exposed surface of the channel containing the fluid, there arises the possibility that heat can bleed from one leg of the serpentine channel to an adjacent leg of the channel, thereby raising the temperature of that adjacent leg in an undesired manner. In order to prevent this undesired occurrence, it is advantageous to include a thermal isolation feature between adjacent channels. Using a thermal isolation feature blocks the undesired lateral flow of heat between adjacent channels, thereby ensuring that most heat flow occurs longitudinally in the channel in the direction of fluid flow where it can provide a signal related to the flow magnitude or perpendicular to the exposed surface of the structure defining the fluid channel into the ambient environment.

A thermal isolation feature for the above purpose may take the form of a region between adjacent legs of the fluid path wherein the thermal conductivity of the thermal isolation feature is very much less than the thermal conductivity of either the flowing fluid, or the channel walls enclosing the fluid, in two adjacent legs of the channel. As discussed above, one method of providing such a thermal isolation region is the use of insulative materials between adjacent legs of the serpentine flow path. Such a region may also advantageously take the form of a void filled with a gas or vacuum wherein the void is located between the walls of the two adjacent fluid channel legs. A vacuum has essentially zero thermal conductivity, while gases including air and sulfur hexafluoride have thermal conductivities which are much less than the thermal conductivities of solid materials, such as plastics, polymers, glasses, and the like.

The thermally isolative void 90 may take the form of a narrow slot created through the substrate, and different slots can be situated at different locations on the substrate structure.

Voids 90 may extend completely through the substrate structure in which the fluidic channels are enclosed. Alternatively, voids 90 may be bounded on one or both planar surfaces of the substrate structure by thin regions which provide mechanical integrity to the substrate structure while constituting only a minor thermal conduction path compared to the thermal conduction path which would be present if voids 90 were not used.

If slots 90 extend entirely through the substrate structure, small support sections 92 are used to maintain the structural integrity of the overall substrate structure. Even when the slots do not extend entirely through the substrate structure, providing such support sections 92 may still be desirable to enhance the strength of the substrate structure. While such support sections 92 do provide a thermal bridge, such section provide only a minor thermal conduction path compared to the thermal conduction path which would be present if voids 90 were not used.

FIG. 12 depicts a substrate structure 94 defining a fluid channel 32 having a serpentine path with a plurality of substantially parallel adjacent path segments 96, 98, 100, 102, 104, 106. As can be seen in FIG. 12, insulative voids 90 are disposed proximate the fluid channel 32 to inhibit transfer of thermal energy from the fluid in channel 32 through the substrate structure 94. Support sections 92 periodically interrupt voids 90 to provide structural strength. The voids 90 have low thermal conductivity and provide thermal isolation between adjacent path segments 96, 98, 100, 102, 104, 106. The support sections 92 provide the substrate structure 94 with structural integrity in the same way that support regions in a stencil keep the stencil from falling apart.

FIG. 13 provides a schematic cross sectional view of two alternative embodiments of insulative voids. Void 90A extends through the entirety of substrate structure 94. The depicted substrate structure 94 includes two outer layers 52, 56 and a middle layer 54. Fluid channel 32 is formed by forming a void in middle layer 54. Similarly, an insulative void 90B can be created by forming a void through middle layer 54. Void 90A which extends entirely through substrate structure 94 can advantageously be formed after joining layers 52, 54, 56 to form substrate structure 94. One advantage of forming a void 90B having a height that is the same as the fluid channel 32 is that it can be formed at the same time as the fluid channel using the same manufacturing technique thereby providing manufacturing efficiencies. While void 90A is open to the ambient atmosphere and will be filled with air, void 90B is enclosed and, if desired, could have a vacuum formed therein or be filled with a gas other than air. It is also noted that the insulative void may take on still other forms. For example, it might be open to the atmosphere at only one end. Alternatively, it might not conform precisely to the height of middle layer 54. For example, it could extend partially into layer 52 or not extend the full extent of middle layer 54. Various other variations on such insulative voids are also possible.

While the exemplary fluid channel 32 is formed on a fluidic chip, larger tubes or conduits could alternatively be employed. Various microfluidic fabrication methods may be employed to manufacture a fluid channel 32 such as soft lithography, traditional lithography, laser or plotter cutting, embossing, injection molding, three-dimensional printing, lamination, extrusion or other suitable method.

Thermographic image device 46 is positioned to capture an image that includes at least a portion of downstream section 42. Advantageously, device 46 is positioned to capture a thermal image that includes both the downstream section 42 and the upstream section 44 of fluid channel 32. As discussed above, in the exemplary embodiment, upstream section 44 of fluid channel 32 upstream of position 40 has a predefined cross section and a predefined flow path and downstream section 42 of fluid channel 32 downstream of position 40 also has a predefined cross section (FIG. 4) and a predefined flow path (FIG. 2).

The material used to form the outer layer facing thermal imaging device 46 may advantageously be selected to facilitate the capture of an image representative of the thermal profile of liquid 24 in channel 32. For example, the layer may be formed out of a material substantially transparent or opaque to thermal radiation in the wavelengths captured in the image. With either approach, it is advantageous if the thermal information can be conveyed rapidly to thermal imaging device 46. Another consideration in the choice of materials is compatibility with the fluid being conveyed. For drug delivery applications, the biocompatibility of the material will need to be acceptable.

For example, the outer layer which faces thermal imaging device 46 may be substantially transparent to infrared light such that the layer acts as a window allowing the thermal imaging device to capture an image of the fluid medication 24 in channel 32 through the outer layer. Advantageously, the material is substantially transparent to radiation having a wavelength of approximately 10 microns. Even more advantageously, the material is substantially transparent to wavelengths between approximately 1 and approximately 50 microns. Various materials may be used to form such a transparent layer such as silicon, polydimethylsiloxane (PDMS), germanium, zinc selenide, silicon nitride and other suitable materials which are transmissive for the range of wavelengths captured by thermal imaging device 46.

Cyclo olefin polymers and copolymers, such as those available under the tradenames Zeonor and Zeonex, may also be used to form a substantially transparent layer. In this regard, it is noted that cyclo olefin polymers and copolymers are not entirely transparent to infrared light in the typical range of thermal imaging devices, a sufficiently thin film of such material will be suitably transparent. Similarly, many materials not typically considered infrared transparent, will be infrared transparent when formed in a sufficiently thin film.

Alternatively, the outer layer which faces thermal imaging device 46 may be substantially opaque to infrared light with the thermal imaging device 46 being positioned to capture an image facing the opaque layer. Advantageously, the opaque layer would have a relatively high thermal conductivity whereby it rapidly conducts heat from the inner (fluid contact) surface of channel 32 to the outer surface facing thermal imaging device 46. This allows the exterior surface of the material to quickly assume a temperature profile representative of the fluid medication 24 in channel 32. It will also advantageously have relatively high surface emissivity. These properties will, in turn, allow the thermal imaging device 46 to obtain thermal information about the fluid medication 24 in channel 32 indirectly. Various materials may be used to form such an opaque layer such as metals, polymers (which may be thin foils such as mylar, PLA, silicones, etc.), ceramics, glass, thermally conductive polymer-ceramic composites and other suitable materials. Metals, which may be in foil or sheet form, can be advantageous because of their high thermal conductivity and biocompatibility. If the selected material does not have a high surface emissivity, a surface treatment may be applied to increase surface emissivity. For example, the surface could be painted black.

Some materials may be transparent, or at least partially transparent, in the range of wavelengths captured by imaging device 46 and also have a high thermal conductivity.

It is additionally noted that, in some applications, one or more coatings, such as an anti-reflective coating, might be advantageously employed on the outer layer facing device 46. The anti-reflective coating may be formed using a silicon-based material or metal composite. Examples of a suitable material for an anti-reflective coating include TiSi, $SiO_2$, $TiO_2$, $MgF_2$, gold, aluminum, ZnSe, ZnS, $BaF_2$, $CaF_2$, or amorphous material transmitting infrared radiation (AMTIR) anti-reflective chalcogenide glasses. AMTIR anti-reflective cholcogenide glass is commercially available from Amorphous Materials, Inc. of Garland. Tex.

Advantageously, the physical size of the fluidic component 32 and the thermal imaging device 46 of fluid sensing system 30 is sufficiently small to be conveniently handled by the end user. In some embodiments, the fluid channel 32 may be mounted on a substrate having an area of approximately 1 $cm^2$. Both larger and smaller sizes, however, may be desirable. For example, some embodiments might have a fluid channel 32 mounted on a substrate having sides as small as 0.5 cm each. If infrared microscopy or special optics are employed, still smaller sizes, wherein the two sides of the substrate are on the order of tens to hundreds of microns, might be obtainable. Alternatively, the substrate might have sides several cm in length or even larger. Other than the cumbersome nature of larger embodiments, there are very few constraints on the upper limit of the size of the system.

The image 47 captured by device 46 is communicated to processor 48. Processor 48 is used to compute at least one output value as a function of the thermal image wherein that output value is representative of a parameter of fluid flow through fluid channel 32. Various different parameters can be determined from a thermographic image. Most directly, the temperature of the fluid medication 24 can be determined using an image 47. Various other parameters that can be determined include the volumetric flow rate of the fluid medication 24 through channel 32, heat capacity of the fluid, pressure of the fluid; viscosity of the fluid and/or density of the fluid. The determination of some of these parameters may require additional information on the system beyond that contained in the thermographic image 47. Such additional information might include the dimensions of fluid channel 32.

It is desirable to automate image acquisition and extraction of the quantities of interest (e.g., flow rate) from the image data. The task of extracting quantities of interest may be performed by computer vision algorithms that can identify regions of interest within a thermal image and track those regions across consecutive frames. As an example, a heated region and/or a boundary between a warmer and hotter region may be identified as a "feature". Such a feature may then be tracked across consecutive frames acquired by the thermal imager. The rate of motion of such features will correspond to the rate of flow of the fluid. Computer vision may be implemented with the use of existing commercial or open-source computer vision software packages. OpenCV and SimpleCV are examples of full-featured, open-source computer vision packages that are appropriate for this application, and which can be implemented on a variety of computing platforms capable of executing code written in c, c++, Python, Java, or similar programming languages. An example of an inexpensive Linux-based computing platform (i.e., processor) capable of executing computer vision code is the Raspberry Pi.

While OpenCV and SimpleCV computer vision packages offer powerful image processing capabilities, in certain embodiments it may be desirable to instead use much simpler image processing algorithms in order to reduce computing power requirements, and enable functionality using lower-cost computing platforms (processors). Examples of some simpler image processing algorithms include thresholding, locating the brightest and/or dimmest pixels within an image, and observing changes of intensity in pixels in a time sequence of images. Since a thermal image may be represented as a two dimensional array of integers, these simple operations do not require specialized computer vision algorithms, and can be performed directly in terms of numerical matrix operations that are integral to most programming languages. The benefit of using full-featured computer vision packages is extended functionality, while the benefit of simpler image processing algorithms is reduction of cost due to reduced computing power requirements.

As mentioned above, the image data acquired by thermal imaging device 46 is communicated to processor 48. Processor 48 may be any suitable processor. One commercially available processor that has low power requirements and which is well suited for use in fluid sensing system 30 is the processing module sold by Intel Corporation under the trademark Edison. Alternatively, custom-designed ASIC (application-specific integrated circuits) or custom-designed FPGA (field-programmable gate array) chips could be used for processor 48.

The output value or values generated by processor 48 is communicated to display 50 in the exemplary embodiment. The output value can be utilized for different purposes depending upon the application. For example, the output value can be communicated to the user of the delivery device 20. This allows the user (or family member, caregiver or other medical care provider) to be informed of the successful delivery of the fluid, e.g., medication, and the quantity of the delivered fluid, or, that a problem in the delivery was encountered. Processor 48 may advantageously log any problems or errors encountered in delivery of the fluid. Successful deliveries of fluid and the details of such deliveries, such as the quantity and time of delivery, could also be logged into a memory module in the processing unit or output to a separate device having a digital memory for recording such data and/or transmitted by wireless or wired communication to a medical professional or other party involved in the care of the patient.

The output value or values generated by processor 48 may also or alternatively be used to provide active feedback to control mechanisms such as a fluid pump, valves, thermal device 38, mixing unit, or other mechanism. Such control feedback can be used to ensure precise delivery of fluid quantities and that the desired conditions of fluid delivery are satisfied.

Advantageously, thermal imaging device 46 is aligned and registered with fluid channel 32 such that each pixel on the sensor of thermal imaging device 46 corresponds directly to a specific point in the field of view. Generally, it will be those pixels which correspond to a specific point in fluid channel 32 can be used to perform analysis of thermal image 47. In some applications, the thermal signature of the structure surrounding fluid channel 32 might also be beneficially employed in the analysis of the thermal image 47. The input of the known geometry of fluid channel 32 and the registration of thermal imaging device 46 with fluid channel 32 is performed before conducting an analysis of acquired images 47.

The temperature of the fluid medication 24 or fluid channel 32 in direct contact with fluid medication 24 can be measured directly at each relevant pixel in the thermal image. The velocity of the fluid flow can be determined in fluid channel 32 in different manners. For example, by using thermal device 38 in a pulsed mode, a slug of heated or cooled liquid can be observed flowing through channel 32 to determine the flow velocity. By using thermal device 38 to provide constant heating or cooling, a steady state temperature profile can be obtained. For a known fluid, these profiles can be correlated to a fluid velocity. FIGS. 5-7 illustrate how the temperature profile of a fluid can vary depending upon the flow velocity when using the same fluid and same thermal input. In this regard, it is noted that, for the same fluid and same heat input, FIG. 5 represents a low flowrate, FIG. 6 represents a medium flowrate and FIG. 7 represents a high flow rate. With proper calibration, these profiles can be used to estimate the fluid velocity. It is noted that, for purposes of graphical simplicity, FIGS. 5-7 have been simplified and been presented in shades of black and gray and do not show the full structure and granularity of an actual thermal image. It is typical, when visually representing a thermal image for viewing by a human user, to use a false color representation wherein several different colors and shades of those colors to more precisely and intuitively represent the different spot temperatures acquired at each pixel location. It is noted that when a thermal image will be processed without human viewing, there is no need to generate a false color image and the generation of a false color image is done simply to provide a readily understandable visual image for a human viewer.

In addition to flowrate, it may also be possible to determine the identity and concentration of the fluid based upon an individual thermal profile. For example, a library of images of different known fluids using a known flow rate and a known heat/cooling input for a given flow channel configuration can be created. Then, a thermal image can be acquired for the fluid in question when that fluid is subject to the same flow rate and heat/cooling input for the same flow channel configuration. The acquired image can then be compared to the library of images to determine which library image most closely matches the acquired image. The fluid in question would then be assumed to have the same characteristics as the fluid for the matched library image. It is thought that this approach could be advantageously employed for applications wherein there would be a limited number of different fluids that might potentially be used with the fluid sensing system. For example, if the fluid sensing system is used with a medicament delivery device, there might be a limited subset of fluids used with the device. In one such application, the device might be expected to be used only with fluids which include insulin or human growth hormone at one of a limited number of predefined concentrations. A thermal image of each of the predefined concentrations of insulin and of each of the predefined concentrations of human growth hormone could be included in the library for comparison with the acquired image.

Characteristics of the fluid can also be obtained by analysis of one or more acquired images instead of matching the images with library images. For example, in a pipe or confined channel, the volumetric flowrate, Q, is defined as the product of fluid velocity and the cross sectional area of the channel. The dimensions, and thus cross sectional area of channel 32 are known, thus, once the fluid velocity within channel 32 is determined, the calculation of a volumetric flow rate is readily obtained. If the volumetric flow rate is known and the elapsed time of the flow is also known, the flow volume, i.e., the volume of fluid which flows past the monitored point during the elapsed time can be easily determined. Unless the device includes some feature which diverts part of the fluid flow, this will also be the volume of fluid which is discharged through the discharge structure 26. When injecting medicaments into a patient, the volume of the medicament discharged through structure 26 will be of significant importance and being able to precisely monitor the discharged volume is a valuable feature.

The flow volume can also be more directly determined using sensing system 30. For example, thermal device 38 can be operated in a pulsed mode to generate one or more slugs of heated or cooled fluid at the beginning of the fluid flow. These slugs can then be monitored to determine how far they travel down the fluid channel. The dimensions of the fluid channel are known, and thus, the volume of displaced fluid from the beginning of the fluid flow to the end of the fluid flow can be readily determined. For example, if a slug of heated/cooled fluid is generated at the start of an injection and a thermal image is taken shortly before or at the beginning of the injection process and at or shortly after the end of the injection process, the position of the heated/cooled slug of fluid can be determined at both the beginning and end of the injection process. The volume of the fluid channel between these two locations will be the volume of the displaced fluid which will also be the volume of the fluid discharged through discharge structure 26 absent any diversionary feature. Because the location of the thermal device 38 is known, it may also be possible to determine the flow volume with a single thermal image. For example, if the heated/cooled slug is generated just before initiating the injection, a single image taken at the end of the injection process to determine the location of the fluid slug may be sufficient. For large flow volumes where the initial heated/cooled fluid slug will be discharged, a series of heated/cooled slugs could be generated and tracked as they pass through the fluid channel.

Alternatively, if the fluid flow can be controlled sufficiently to maintain a substantially constant fluid flow, a heated or cooled slug of fluid could be generated during the course of the fluid flow. An image could be taken at two separate times, at a known time interval, to determine the distance the slug of fluid had traveled during that time period. This would provide a value for the fluid velocity, which, in turn, could be used to determine the volumetric flow rate because the cross sectional area of the channel is known. Once the volumetric flow rate is known, if the fluid flow is held constant for the entire time the fluid is discharged and the time period for the fluid discharge is known, the total volume of fluid discharged could be easily determined. It may also be possible to use only a single image to determine the volumetric flow rate if an image is captured at a known time interval after the creation of the heated/cooled slug of fluid. By determining how far the slug traveled in a channel of known cross sectional area during the time period between generation of the heated/cooled slug and the capture of the image, the volumetric flow rate can be determined. Once the volumetric flow rate is determined, the total discharge volume can be determined as described above.

Spot measurements of the rate of heating/cooling of the fluid by thermal device 38 can be used to provide a direct measurement of the specific heat capacity of the liquid flowing in channel 32. In other words, by taking multiple temperature readings at a selected pixel location over a known time interval and knowing the amount of thermal energy supplied or removed by thermal device 38, the heat capacity of fluid medication 24 can be calculated. Heat capacity is given by the equation: $C=Q/\Delta T$ where C is the heat capacity, Q is the heat energy provided to (or removed from) the material and $\Delta T$ is the change in temperature. For a resistor-type thermal device 38, Q may be equated to the energy applied to the resistor, $Q=(V^2/R)*t$, where V is the voltage applied to the resistor, R is the resistance of the resistor and t is duration of the applied power. By observing the temperature change in fluid medication 24 proximate to location 40 before and after a known voltage is applied to a resistor of known resistance for a known duration, the heat capacity of fluid medication 24 can be determined. The thermal characteristics of flow channel 32 can be calibrated for in advance using a fluid with a known heat capacity.

Although the heat generated by the resistor can be determined using the formula set forth above, there generally will be some thermal loss and not all of the generated heat will be transferred to the fluid. This heat loss will need to be accounted for when employing this method. For example, it may be possible to calibrate the device to account for the heat loss provided that the original temperature of the fluid and the ambient temperature are within an intended temperature range.

The determination of the heat capacity of fluid medication 24 can be particularly useful in applications where it is desirable to confirm the identity or concentration of a medication being delivered through channel 32. For example, the heat capacity of a fluid will typically vary as the concentration of an active medicine in a liquid carrier (e.g., water) is varied. By measuring both the total volume delivered and the concentration of the medication, the correct dosage of a delivered medicine can be confirmed.

Instead of calculating a heat capacity, a library of images of different known fluids using a known flow rate and a known heat/cooling input for a given flow channel configuration could alternatively be used to identify the fluid and the concentration of the active ingredient in the fluid as discussed above.

The measured heat capacity and/or use of a library of images might also be used to monitor the presence or absence of known markers deliberately added by a drug manufacturer or of contaminants resulting from counterfeit manufacturing processes that generate imitation drugs which do not satisfy the manufacturer's original specifications. Unique thermal features could alternatively or additionally be added to the reservoir, which may have a seal that has to be broken when performing the first injection, to confirm the authenticity of the reservoir and its contents.

The analysis of the thermal images 47 can also be used to identify obstructions and foreign matter in the fluid flow. Foreign matter, air bubbles and other obstructions within the fluid flow will have different thermal characteristics, e.g., heat capacity, and will generally show up as discrete objects having a different temperature than the immediately surrounding fluid. Such objects will generally be easy to identify in the thermal image. In some applications, the volume of such items can be subtracted from the total volume delivered to provide a more accurate measurement of volume of intended fluid that was delivered. The presence of air bubbles in the fluid might also indicate the presence of a leak. An appropriate message might be communicated to the user or controller upon the detection of such bubbles in addition to making corrections to the determination of flow volume.

Figure 8:
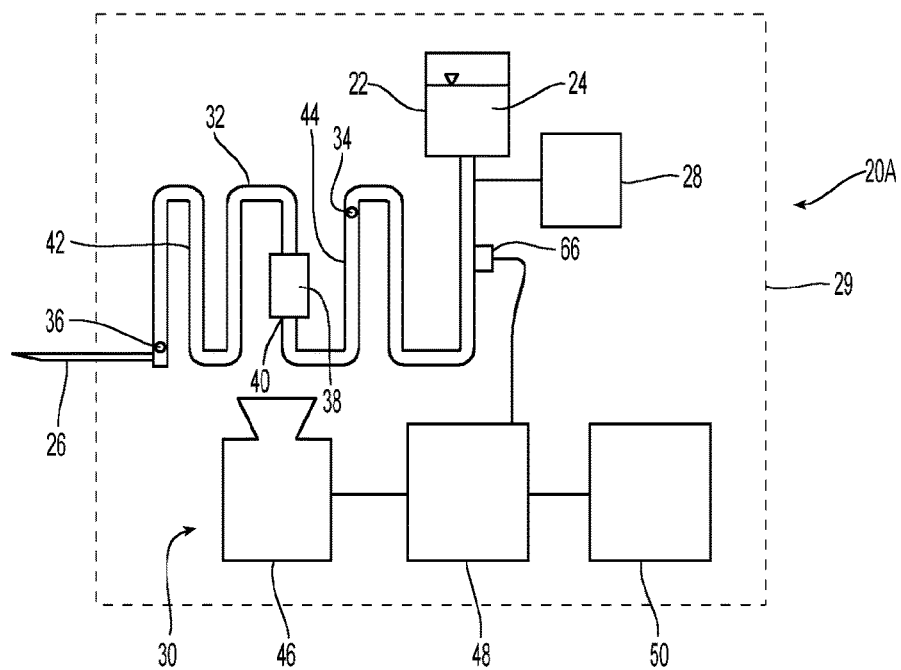
FIG. 8 is a schematic representation of an alternative delivery device employing a fluid sensing system.

Various other parameters can be determined using advanced image analysis such as fluid viscosity, fluid pressure and fluid density. In general the motion of an incompressible viscous fluid is described by the Navier-Stokes equations. These equations can be solved numerically and their solutions compared to the image data. It is known to use the Navier-Stokes equations to solve for one or more of the fluid velocity, pressure and kinematic viscosity when the boundary conditions for the fluid flow are known. The Reynolds number (Re) of a liquid can be derived from the Navier-Stokes equations and is useful for describing when fluid flow is laminar or turbulent. When using such multi-variable equations to determine a fluid property, it may be desirable or possibly necessary to include a second sensor to measure an additional fluid property such as pressure. An embodiment having such a second sensor is illustrated in FIG. 8.

Low Reynolds numbers correspond with laminar flow where viscous forces dominate and fluid flow is smooth with constant motion. High Reynolds numbers correspond with turbulent flow dominated by inertial forces and which result in unstable flow patterns. For flow through a pipe, Re is defined as: $Re=(\rho v D_H)/\mu=(v D_H)/v=(Q D_H)/(v A)$ where $D_H$ is the hydraulic diameter of the pipe, Q is the volumetric flowrate, A is the pipe cross sectional area, v is the mean velocity of the fluid, $\mu$ is the dynamic viscosity, v is the kinematic viscosity and $\rho$ is the density of the fluid.

Thermal images acquired by thermal imaging device 46 allow for the direct visualization of whether the fluid flow is laminar or turbulent. This provides the possibility of estimating the Reynolds number based upon the image. In this regard, it is noted that as the Reynolds number increases the pattern of the turbulence will be impacted and thereby provides for the possibility of estimating the Reynolds number based upon the severity of the turbulence. Once the Reynolds number is known, given a known flow rate, channel geometry and fluid density, the viscosity can be calculated. Alternatively, fluid density may be estimated if the viscosity is known. If both viscosity and fluid density are known, the pressure can be determined. Similarly, depending on the known variables it can be possible to calculate the other variables present in the different Reynolds number relationships.

It is further noted, that fluid density is also related to the concentration of a dissolved substance in a fluid carrier. For example, if the identity of the fluid and dissolved substance is known, once the density of the fluid is determined, the concentration of the substance in the fluid (e.g., the concentration of an active ingredient in a medicament) could then be determined from the density. Alternatively, if the identity and concentration of the fluid is known, then the density can be determined.

It is further noted that by configuring fluid channel 32 to have a number of different sections of varying dimensions such that, for a given fluid viscosity and flow rate, the onset of turbulence can be expected in at least one of the sections but not others, the Reynolds number can be more effectively determined by a simple visual inspection of the thermal image to determine which sections of fluid channel 32 have turbulent flow and which do not.

In addition to the detection of turbulent flow, fluid properties can potentially be determined based on observations of convective or buoyant flow or diffusion. Viscosity, for example, may be measured by observing diffusive broadening of a heated flowing band within a channel under laminar or turbulent conditions. In this regard, it is noted that by using thermal device 38 in a pulsed mode, a slug of heated or cooled liquid can be generated and images showing the sequential broadening and other changes in the shape of this slug of liquid can be captured with thermal imaging device 46.

Some relevant quantities that are useful to describe convective and diffusive flow are the Rayleigh number, Ra; the Grashof number, Gr, and the Prandtl number Pr (the last being an intrinsic property of a fluid). These, and other, parameters may be estimated from thermal imaging and define relationships between fluid properties such as viscosity, diffusivity, thermal conductivity, specific heat, volume expansion coefficient and fluid density.

When two fluids, or a fluid and a solid, of different temperatures are mixed together, the thermographic image of the mixing might also be useful in determining properties of the fluid flow. For example, a slug of cooled or heated fluid could be generated with thermal device 38 and its mixing with the surrounding fluid observed using thermal imaging device 46. Alternatively, a second fluid line could interject a second fluid at a different temperature at a point downstream of point 40. In such an application, the second fluid could potentially be fluid medication 24 which is routed to downstream section 42 through a second conveyance which does not route the fluid past thermal device 38. Similarly, a warm fluid could be used to dissolve a cold solid or a warm fluid could be mixed with cold particles. For example, such solid particles might be small particles that take the form of a powder.

It is further noted that when mixing a liquid with particulate solids to form the fluid that is the subject of the sensor system, such solids may remain suspended as solids in the liquid or be dissolved in the liquid to form a solution. As mentioned above with regard to unwanted air bubbles, the subject fluid might also take the form of a mixture of liquid and gas whether or not the gas is intentionally introduced. For example, the purposeful introduction of a gas could be used to manage the initial temperature of the fluid.

Another potential use of fluid sensing system 30 is the verification/authentication of reservoir 22. For example, fluid sensing system 30 could be used for the authentication of a disposable medication cartridge containing one or more doses of medication. This could be accomplished by placing reservoir 22 in the field of view of thermal imaging device 46 and manufacturing reservoir 22 to have a characteristic optical, thermal and/or heat capacity signature that could be verified by the analysis of the thermal image captured by device 46. This would allow for the identification and verification of the manufacturer, type of drug, etc. For instance, a pattern invisible to the naked eye that is more or less thermally emissive in the range of wavelengths detected by device 46, or more or less thermally conductive could be detected in the thermal images captured by device 46. For example, a metal, ceramic or polymer material could integrated into a reservoir wall formed out of a different material with differing thermal properties to form the identifying pattern. Such identification procedures would be useful for anti-counterfeiting efforts.

It may also be possible to measure pressure by observing temperature changes in a sealed reservoir 22 or other vessel in communication with fluid channel 32 and filled entirely with gas or both liquid and gas. If the reservoir/vessel was expandable, expansion of the reservoir/vessel could be used to determine pressure. Alternatively, changes in gas pressure could result in observable temperature changes potentially observable using thermal imaging device 46.

It is also possible to utilize a second fluid sensor in combination with thermal imaging device 46. While temperature and flow rate, flow volumes readily obtained using thermal imaging device 46, obtaining accurate measurements of viscosity and density using only a thermal imaging device 46 presents greater difficulties as discussed above. As a result, such additional values might not be obtainable or have the desired accuracy when using only a thermal imaging device 46. Utilizing a second fluid sensor to measure a property of the fluid provides two measurements which can be used in known fluid formulas to more reliably and accurately determine fluid properties such as viscosity, density and fluid identity.

FIG. 8 schematically depicts an example of such a system employing an additional sensor 66. Sensor 66 is advantageously a miniaturized sensor such as a micro electromechanical system (MEMS) fluid pressure sensor. Such small scale fluid pressure sensors are commercially available and typically provide a sensor and signal conditioning electronics on a single chip thereby providing a small scale fluid sensor. Sensor 66 is coupled with controller 48 whereby the sensed fluid pressure can be communicated to controller 48. As discussed above, by obtaining both a sensed fluid pressure and one or more thermographic images, the determination of fluid properties is enhanced. The system 20A depicted in FIG. 8 is the same as that shown in FIG. 1 except for the addition of sensor 66. Although a pressure sensor is shown in the embodiment of FIG. 8A, other types of sensors could also be used depending upon the type of application for which the device will be employed.

Depending upon the particular application, it may only be necessary to obtain a single pressure measurement at the same time as the capture of a thermographic image. In other applications, it may be desirable to continuously monitor the pressure. In the illustrated embodiment, the location of the pressure sensor is shown upstream of inlet 34. In alternative embodiments, however, sensor 66 could be coupled with channel 32 proximate thermal device 38 or elsewhere on channel 32 or between outlet 36 and the discharge structure 26. In other words, the sensor may be operably coupled with the fluid medication being transferred from the reservoir to the discharge structure at any point between the reservoir and discharge structure provided that the arrangement allows for obtaining the desired measurement. Depending on the type of sensor, it may either directly or indirectly obtain the desired measurement.

Figure 8A:
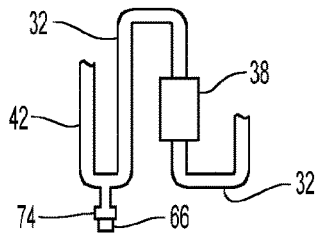

For example, FIG. 8A depicts a MEMS pressure sensor 66 coupled with a side chamber 74 that is in fluid communication with main fluid channel 32 in the downstream section 42 of channel 32. Such a side chamber is suitable for use with some types of sensors under certain conditions, however, it may not be suitable for all sensors or under all flow conditions.

Figure 9:
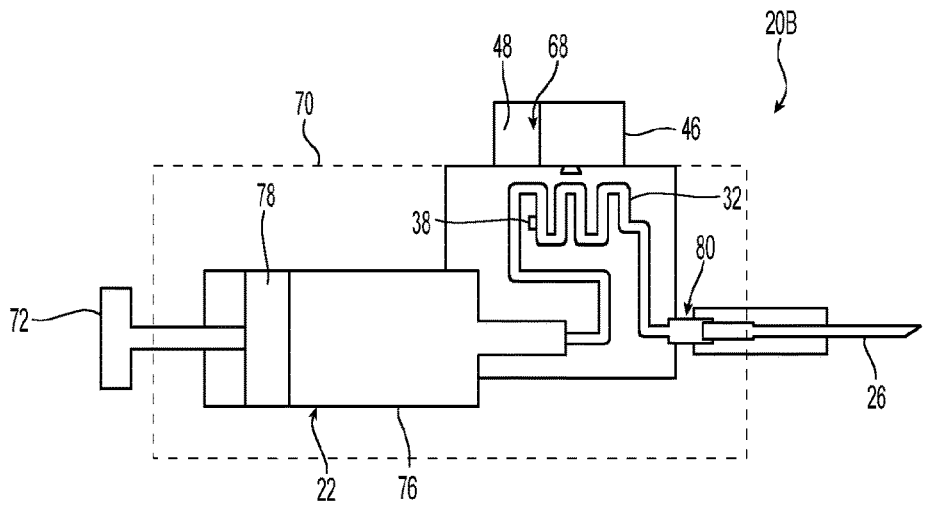
FIG. 9 is a schematic representation of another alternative delivery device employing a fluid sensing system.

FIG. 9 depicts a medical delivery device 20B which utilizes a reusable electronics package 68 while much if not all of the remainder of the system is disposable. Electronics package 68 includes the thermal imaging device 46 and controller 48. It would also include the display 50 if a display is to be used with the device. Housing 70 may be either reusable or disposable. If a simple and inexpensive arrangement, such as a manual plunger 72, is used for the driving mechanism, it may be advantageous for housing 70 and plunger 72 to be disposable. If a more elaborate driving mechanism, such as a battery powered motor, is used, it will generally be desirable for the housing and driving mechanism to be reusable.

If a disposable housing 70 is used, electronics package 68 is detachably secured to housing 70 using a snap fit, threaded engagement or other suitable arrangement. If the housing is intended to be reused, electronic package 68 may be permanently secured to the housing.

The reservoir 22 used in the embodiment of FIG. 9 includes a cylindrical barrel 76 and a piston 78. The advancement of piston 78 by the driving mechanism expels the fluid medication through the opposite end of barrel 76 and into the fluid channel 32. Fluid channel 32 may be formed on a chip that is mounted on an exterior surface of reservoir 22 as schematically depicted in FIG. 9. Fluid channel 32 might also be mounted directly on the exterior of reservoir 22. Both the reservoir 22 and fluid channel 32 may be disposable. The discharge structure 26 may take the form of a hollow needle adapted to inject a fluid into a living organism. Advantageously, discharge structure 26 is disengageable from the medication delivery device and is thereby disposable after a single use.

Cooperating Luer fittings on the fluid channel 32 and the needle assembly 26 allow the needle assembly to detached after a single use and replaced with a new needle assembly. The use of Luer fittings to attach injection needles to syringes and allow for the separate disposal of a used needle are well known to those having ordinary skill in the art. This arrangement allows for the use of a new needle for each injection from a reservoir 22 that contained more than one dosage when originally filled. It is additionally noted that the fluid medication 24 used with the illustrated embodiments is a liquid medication.

As mentioned above, both reservoir 22 and fluid channel 32 may be disposable. In this regard it is noted that an electrical resistor mounted on fluid channel 32 would also generally be discarded with the reservoir and fluid channel 32 if an electrical resistor was used as the thermal device 38. In such an embodiment, the surface or substrate on which channel 32 and the electrical resistor was mounted could have exposed electrical contacts that would be abutted into electrical communication with similar contacts on electronic package 68 or on housing 70. For example, if a non-electrically powered drive mechanism was used, the contacts could be located on electronic package 68 which would generally include a battery for powering the electronics mounted therein and this battery could also be used for supplying electrical current to the electrical resistor acting as a thermal device. If, instead, a battery powered motor was installed in housing 70 and used as the drive mechanism, electrical contacts could be mounted in housing 70 to couple the electrical resistor with the batteries powering the drive mechanism 28.

Once the contents of reservoir 22 are depleted, the disposable components of the system are discarded. For some embodiments, this may include both the reservoir 22 and fluid channel 32. For other embodiments, it might also include housing 70 and drive mechanism 28. For example, if the drive mechanism were a polymeric manually operable plunger 72, it may be cost effective to dispose of the plunger at the same time as the reservoir 22.

The embodiment 20B includes a fluid channel 32 supported on reservoir 22. Alternative arrangements, however, are also possible. For example, fluid channel 32 could be supported on the needle assembly. For applications, however, where the needle assembly will be discarded after each use and the reservoir holds more than one dosage, mounting the fluid channel 32 on the needle assembly will generally not be the most desirable. It is also possible for the fluid channel 32 arrangement to be separable from both the reservoir 22 and the discharge structure 26. This arrangement may, however, require the use of mating Luer fittings at both the reservoir 22 to fluid channel 32 interface and at the fluid channel 32 to discharge structure 26 interface. By permanently mounting the fluid channel 32 on reservoir 22, only the fluid channel 32 to discharge structure 26 interface would require Luer fittings to allow for the separate disposal of the discharge structure 26 after each use.

While several of the components of the fluid sensing system can be cost-effectively formed as disposable components, it will generally be desirable for the electronics package 68 to be re-usable. By designing the electronics package to be non-destructively separable from the disposable components of the system, the electronics package can be conveniently re-used after detachment and disposal of the disposable components. Generally, this will mean that the thermal imaging device 46 and processor 48 are non-destructively separable from the reservoir 22 and fluid channel 32. If the system includes a display 50, it will generally be part of the re-usable electronics package and also be non-destructively separable from the disposable components. As mentioned above, some of the other components may be either disposable or re-usable. For example, the housing 70 and driving mechanism may be either re-usable or disposable. If such components are disposable, it will be advantageous for the electronics package 68 to be non-destructively separable from the housing and driving mechanism. If these components are re-usable, it may still be desirable to have the electronics package 68 be non-destructively separable from these components so that if the driving mechanism fails, it would not be necessary to replace the electronics package when replacing the driving mechanism.

Figure 10:
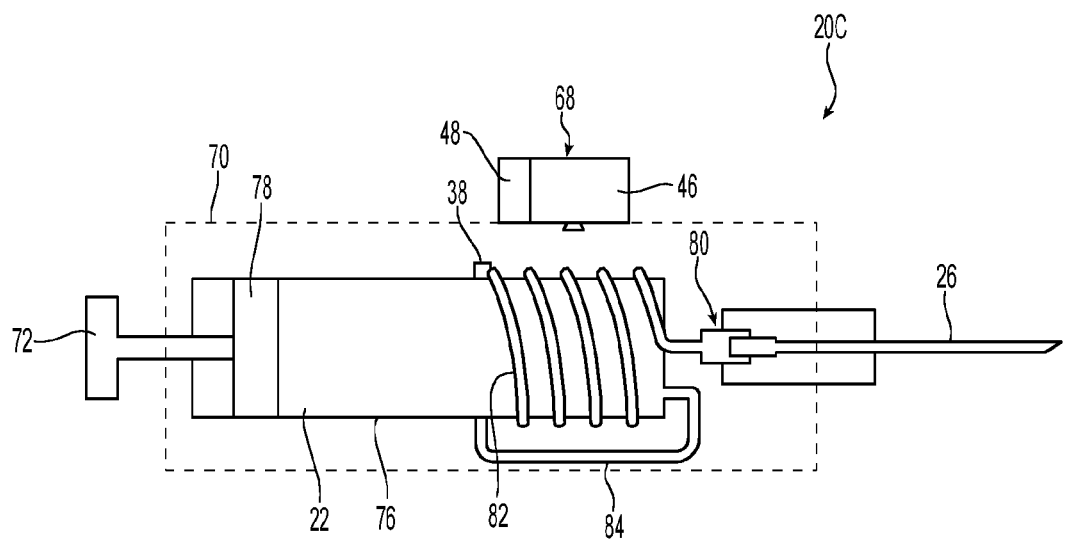
FIG. 10 is a schematic representation of yet another alternative delivery device employing a fluid sensing system.

FIG. 10 is generally similar to embodiment of FIG. 9 but uses a different fluid channel. In this embodiment 20C, the fluid channel is wrapped around columnar barrel 76 of reservoir 22 to form a helical coil 82. In this embodiment, barrel 76 has a cylindrical shape, however, other columnar barrels having an elongate shape, for example, an elongate reservoir having a rectangular cross section, could also be used. Helical coil 82 is formed out of a thin walled tube which is either heat conductive or generally transparent to the radiation in the wavelengths captured by the thermal imaging device 46. Helical coil 82 can be secured in place with adhesive or by other suitable means.

A length of tubing 84 extends rearwards from the distal end of reservoir 22 where the reservoir discharges into the tubing. The tubing is then wrapped around the barrel 76 of reservoir 22 progressing in the distal direction. Proximate the distal end of reservoir 22, the tubing has a fitting for engagement with a cooperating fitting on the injection needle assembly forming discharge structure 26. In the illustrated embodiment, the fittings are Luer fittings. Similar to the embodiment 20B of FIG. 9, reservoir 22 and fluid channel 32 of embodiment 20C can be disposable with needle assembly 26 also being separately disposable.

A significant fraction of the fluid channel 32 that forms helical coil 82 is hidden from view of the thermal imaging device 46 by barrel 76 of reservoir 22. Those portions of helical coil 82 which are in the line-of-sight of thermal imaging device 46 form discrete segments of fluid channel 32. In other words, thermal imaging device 46 is positioned to capture discrete discontinuous portions of the downstream section of fluid channel 32. Thermal device 38 can be positioned such that all of the discrete portions of fluid channel 32 captured by thermal imaging device 46 are downstream of thermal device 38, or, it may be positioned so that thermal imaging device 46 captures discrete portions of fluid channel 32 both upstream and downstream of thermal device 38. Similarly, thermal device 38 may be positioned to be in the field of view of thermal imaging device 46 or hidden from view.

One advantage provided by the use of fluid channel formed into a helical coil 84 is that the distance from the inlet to the outlet of the fluid channel 32 is greater than if the entirety of the fluid channel 32 was in the field of view of the camera. When forming only a single heated slug of fluid, this arrangement provides a greater length of fluid channel 32 for the slug to travel through before exiting the field of view of thermal imaging device 46 in comparison to a serpentine or spiral shaped fluid channel.

It is noted that while the end point of the fluid slug that will be used to determine the final length of travel for the slug in such an embodiment may be hidden from view by the barrel 76 of reservoir 22, with proper calibration, the overall thermal profile of the fluid should allow for the determination of the final position of the slug even when it is hidden from view behind reservoir 22.

Figure 11:
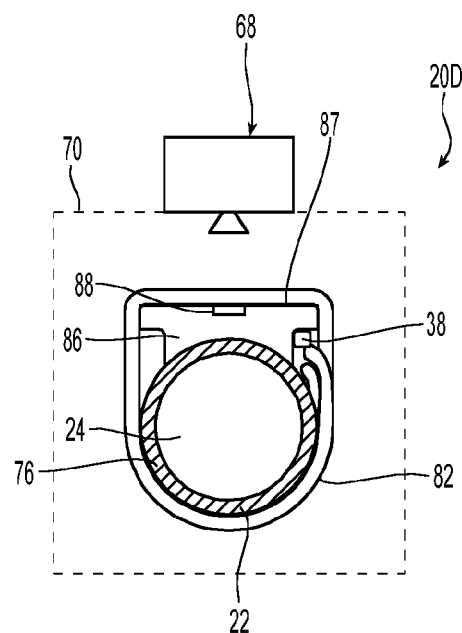
FIG. 11 is a schematic representation of still another alternative delivery device employing a fluid sensing system.

FIG. 11 illustrates an embodiment 20D that is similar to 20C but wherein a projection 86 has been formed on barrel 76 of reservoir 22 to hold that portion of the fluid channel 32 which is in the field of view of thermal imaging device 46 in a substantially planar configuration to thereby simplify the analysis of the thermal images.

The reservoir in this embodiment still has a columnar shape and fluid channel 32 which is wrapped about that portion of the reservoir having projection 86 extending therefrom a defines a helical coil. Although the shape of reservoir 22 is not perfectly cylindrical and fluid channel 32 conforms to the planar surface 87 defined by projection 86, fluid channel 32 is still wrapped about a columnar structure and advances axially along the columnar structure with each winding about the columnar structure and, thus, is helical for purposes of the present application.

Also visible in FIG. 11 is a feature 88 with unique thermal signature such as a uniquely shaped metal component embedded in a polymeric material forming projection 86. Advantageously, feature 88 is positioned on reservoir 22 such that it falls within the field of view of thermal imaging device 46 when reservoir 22 is installed in housing 70. Alternatively, a void or some other thermally identifiable feature in reservoir could provide the unique thermal signature. As mentioned above, the use of such an item with a unique thermal signature embedded in reservoir 22 can be used to authenticate and/or identify reservoir 22 and its contents.

While this invention has been described as having an exemplary design, the present invention may be further modified within the spirit and scope of this disclosure. This application is therefore intended to cover any variations, uses, or adaptations of the invention using its general principles.

What is claimed is:

1. A fluid sensing system for a medication delivery device, the medication delivery device including a reservoir adapted to contain a supply of a fluid medication, and a discharge structure through which the fluid medication is discharged from the medication delivery device, the discharge structure being adapted to introduce the fluid medication into a patient; the fluid sensing system being disposed on the medication delivery device and comprising:

a fluid channel communicating the fluid medication from an inlet to an outlet, the inlet being in fluid communication with the reservoir with the reservoir being disposed upstream of the inlet, and the outlet being in fluid communication with the discharge structure with the discharge structure being disposed downstream of the outlet;

a thermal device operably coupled with the fluid channel at a first position between the inlet and the outlet whereby thermal energy is transferable between the thermal device and the fluid medication flowing in the fluid channel at the first position and wherein a downstream section of the fluid channel downstream of the first position has a predefined cross section and a predefined flow path;

a thermal imaging device positioned to capture a thermal image of at least a portion of the downstream section of the fluid channel; and a processor coupled with the thermal imaging device and configured to determine, based on at least one thermal image, at least one output value that is representative of at least one property of the fluid medication and/or the fluid flow in the fluid channel, wherein the at least one output value includes at least one of a flow volume of the fluid medication, a flow rate of the fluid medication, an identity of the fluid medication, and a concentration of a substance in the fluid medication.

2. The fluid sensing system of claim 1 wherein the fluid medication is a liquid, and the processor is configured to determine the at least one output value further based on a dimension of the downstream section of the fluid channel.

3. The fluid sensing system of claim 1 wherein an upstream section of the fluid channel upstream of the first position has a predefined cross section and a predefined flow path and wherein the thermal imaging device is positioned to capture a thermal image including at least a portion of the upstream section in addition to the portion of the downstream section.

4. The fluid sensing system of claim 3 wherein the downstream section and the upstream section of the fluid channel define a serpentine flow path.

5. The fluid sensing system of claim 1 wherein the fluid channel is disposed on a substantially planar first layer of material.

6. The fluid sensing system of claim 5 further comprising second and third layers of material defining the fluid channel, the first, second and third layers each having a substantially consistent thickness; the second layer being disposed on the first layer and having a void defining the fluid channel; the third layer being disposed on the second layer opposite the first layer whereby the first layer and the third layer enclose the void defined by the second layer.

7. The fluid sensing system of claim 6 wherein one of the first and third layers is a glass substrate.

8. The fluid sensing system of claim 6 wherein the second layer has a thickness within a range of 100 μm to 500 μm.

9. The fluid sensing system of claim 8 wherein the fluid channel has a height substantially equivalent to the thickness of the second layer and a width of approximately 2 mm.

10. The fluid sensing system of claim 6 wherein one of the first and third layers is a thin film layer.

11. The fluid sensing system of claim 10 wherein the thin film layer is a polylactic acid film.

12. The fluid sensing system of claim 6 wherein the first layer is a layer substantially transparent to infrared light and the thermal imaging device is positioned to capture an image facing the first layer.

13. The fluid sensing system of claim 12 wherein the first layer is formed out of a material selected from the group consisting of silicon, polydimethylsiloxane (PDMS), germanium, zinc selenide, silicon nitride, a thin film cyclo olefin polymer and a thin film cyclo olefin copolymer.

14. The fluid sensing system of claim 6 wherein the first layer is a thermally conductive layer substantially opaque to infrared light and the thermal imaging device is positioned to capture an image facing the opaque layer.

15. The fluid sensing system of claim 14 wherein the first layer is formed out of a material selected from the group consisting of metals, polymers, ceramics, glass, and polymer-ceramic composites.

16. The fluid sensing system of claim 1 wherein the thermal device is thermally coupled with an exterior surface of the fluid channel whereby thermal energy is transferred between the thermal device and the fluid medication through a wall of the fluid channel.

17. The fluid sensing system of claim 16 wherein the thermal device and thermal imaging device are positioned on opposite sides of the fluid channel.

18. The fluid sensing system of claim 1 wherein the thermal device communicates thermal energy to the fluid medication in the fluid channel to thereby increase the temperature of the fluid medication.

19. The fluid sensing system of claim 18 wherein the thermal device is an electrical resistor.

20. The fluid sensing system of claim 1 wherein the at least one output value includes a flow volume of the fluid medication.

21. The fluid sensing system of claim 1 wherein the at least one output value further includes at least one of a temperature of the fluid medication, a heat capacity of the fluid medication, a pressure of the fluid medication, a viscosity of the fluid medication and a density of the fluid medication.

22. The fluid sensing system of claim 1 wherein the thermal imaging device is spaced from and fixed relative to the fluid channel.

23. The fluid sensing system of claim 22 wherein the thermal imaging device captures a two-dimensional image defining an aspect ratio and wherein the fluid channel is disposed in a plane and defines a serpentine flow path between the inlet and the outlet; the serpentine flow path defining an overall length and overall width in the plane wherein the ratio of the overall length and overall width are substantially equivalent to the aspect ratio and the thermal imaging device is positioned to capture an image containing substantially all of the serpentine flow path between the inlet and the outlet.

24. A fluid sensing system for a medication delivery device, the medication delivery device including a reservoir adapted to contain a supply of a fluid medication, and a discharge structure through which the fluid medication is discharged from the medication delivery device, the discharge structure being adapted to introduce the fluid medication into a patient the fluid sensing system being disposed on the medication delivery device and comprising:
a fluid channel communicating the fluid medication from an inlet to an outlet, the inlet being in fluid communication with the reservoir with the reservoir being disposed upstream of the inlet, and the outlet being in fluid communication with the discharge structure with the discharge structure being disposed downstream of the outlet;
a thermal device operably coupled with the fluid channel at a first position between the inlet and the outlet whereby thermal energy is transferable between the thermal device and the fluid medication flowing in the fluid channel at the first position and wherein a downstream section of the fluid channel downstream of the first position has a predefined cross section and a predefined flow path;
a thermal imaging device positioned to capture a thermal image of at least a portion of the downstream section of the fluid channel; and
a processor coupled with the thermal imaging device and configured to determine, based on at least one thermal image, at least one output value that is representative of a property of the fluid medication and/or the fluid flow in the fluid channel, wherein the fluid channel forms a helical coil and the thermal imaging device is positioned to capture discrete discontinuous portions of the downstream section of the fluid channel.

25. The fluid sensing system of claim 24 wherein the reservoir has a columnar shape and the helical coil is wrapped about at least a portion of the reservoir.

26. The fluid sensing system of claim 1 further comprising a fluid pressure sensor, the fluid pressure sensor being operably coupled with the fluid medication between the reservoir and the discharge structure, the fluid pressure sensor being adapted to measure a fluid pressure of the fluid medication.

27. The fluid sensing system of claim 26 wherein the second sensor is a fluid pressure sensor.

28. The fluid sensing system of claim 1 wherein the discharge structure is disengageable from the medication delivery device and is thereby disposable after a single use.

29. The fluid sensing system of claim 28 wherein the fluid channel is supported on the reservoir and the thermal imaging device and processor are non-destructively separable from the reservoir and the fluid channel whereby the reservoir and the fluid channel are disposable after the contents of the reservoir have been depleted.

30. The fluid sensing system of claim 1 wherein the discharge structure is a hollow needle adapted to be inserted into a living organism whereby the fluid medication can be injected into the living organism.

31. The fluid sensing system of claim 1 wherein the reservoir includes a feature having a thermally unique signature and whereby the identity or authenticity of the reservoir and its contents are detectable with the thermal imaging device.

32. A fluid sensing system for a medication delivery device, the medication delivery device including a reservoir adapted to contain a supply of a fluid medication, and a discharge structure through which the fluid medication is discharged from the medication delivery device, the discharge structure being adapted to introduce the fluid medication into a patient the fluid sensing system being disposed on the medication delivery device and comprising:
a fluid channel communicating the fluid medication from an inlet to an outlet, the inlet being in fluid communication with the reservoir with the reservoir being disposed upstream of the inlet, and the outlet being in fluid communication with the discharge structure with the discharge structure being disposed downstream of the outlet;

a thermal device operably coupled with the fluid channel at a first position between the inlet and the outlet whereby thermal energy is transferable between the thermal device and the fluid medication flowing in the fluid channel at the first position and wherein a downstream section of the fluid channel downstream of the first position has a predefined cross section and a predefined flow path;

a thermal imaging device positioned to capture a thermal image of at least a portion of the downstream section of the fluid channel; and a processor coupled with the thermal imaging device and configured to determine, based on at least one thermal image, at least one output value that is representative of a property of the fluid medication and/or the fluid flow in the fluid channel, wherein a substrate structure defines the fluid channel and wherein the substrate structure further defines at least one insulative void.

33. The fluid sensing system of claim 32 wherein the insulative void defines a slot extending entirely through the substrate structure.

34. The fluid sensing system of claim 32 wherein the fluid channel defines a serpentine path having a plurality of parallel path segments and wherein the at least one insulative void comprises a plurality of insulative voids with at least one of the plurality of insulative voids being disposed between each pair of adjacent path segments.

* * * * *

UNITED STATES PATENT AND TRADEMARK OFFICE
CERTIFICATE OF CORRECTION

PATENT NO. : 10,537,676 B2
APPLICATION NO. : 15/766859
DATED : January 21, 2020
INVENTOR(S) : Phillip W. Barth et al.

It is certified that error appears in the above-identified patent and that said Letters Patent is hereby corrected as shown below:

In the Claims

In Column 26, Line 5, Claim 1, after "communication" 2nd occurrence delete "with the reservoir".

In Column 26, Line 7, Claim 1, after "communication" 2nd occurrence delete "with the discharge structure".

In Column 27, Line 62, Claim 24, delete "patient" and insert -- patient, --, therefor.

In Column 27, Line 66, Claim 24, after "communication" 2nd occurrence delete "with the reservoir".

In Column 28, Line 1, Claim 24, after "communication" 1st occurrence delete "with the discharge structure".

In Column 28, Line 59, Claim 32, delete "patient" and insert -- patient, --, therefor.

In Column 28, Line 63, Claim 32, after "communication" 2nd occurrence delete "with the reservoir".

In Column 28, Line 65, Claim 32, after "communication" 2nd occurrence delete "with the discharge structure".

Signed and Sealed this
Tenth Day of March, 2020

Andrei Iancu
*Director of the United States Patent and Trademark Office*